US011801334B2

(12) United States Patent
Orava et al.

(10) Patent No.: US 11,801,334 B2
(45) Date of Patent: Oct. 31, 2023

(54) PLATELET RICH PLASMA SEPARATION KIT

(71) Applicant: Enso Discoveries, LLC, Manhattan, KS (US)

(72) Inventors: James Corey Orava, Manchester, VT (US); Patrick Joseph Farley, Manhattan, KS (US)

( * ) Notice: Subject to any disclaimer, the term of this patent is extended or adjusted under 35 U.S.C. 154(b) by 407 days.

(21) Appl. No.: 17/028,080

(22) Filed: Sep. 22, 2020

(65) Prior Publication Data

US 2021/0085841 A1     Mar. 25, 2021

Related U.S. Application Data

(60) Provisional application No. 62/904,970, filed on Sep. 24, 2019.

(51) Int. Cl.

| A61M 1/02 | (2006.01) |
|---|---|
| A61M 5/32 | (2006.01) |
| A61M 5/36 | (2006.01) |
| A61M 5/38 | (2006.01) |
| A61M 5/46 | (2006.01) |
| A61M 5/178 | (2006.01) |
| A61M 5/165 | (2006.01) |

(52) U.S. Cl.
CPC .......... *A61M 1/029* (2013.01); *A61M 1/0209* (2013.01); *A61M 1/0218* (2014.02); *A61M 1/0236* (2014.02); *A61M 1/0259* (2013.01); *A61M 5/165* (2013.01); *A61M 5/178* (2013.01); *A61M 5/32* (2013.01); *A61M 5/36* (2013.01); *A61M 5/38* (2013.01); *A61M 5/46* (2013.01); *A61M 2005/1652* (2013.01); *A61M 2202/0415* (2013.01); *A61M 2202/0427* (2013.01); *A61M 2209/04* (2013.01)

(58) Field of Classification Search
CPC .. A61M 1/029; A61M 1/0209; A61M 1/0218; A61M 1/0236; A61M 1/0259; A61M 5/165; A61M 5/178; A61M 5/32; A61M 5/36; A61M 5/38; A61M 5/46; A61M 2005/1652; A61M 2202/0415; A61M 2202/0427; A61M 2209/04
See application file for complete search history.

(56) References Cited

FOREIGN PATENT DOCUMENTS

WO     WO 99/01198     *  1/1999

OTHER PUBLICATIONS

The photo version of the same sterile PRP separation kit that was submitted in the IDS submission on Sep. 22, 2020, but not considered by the Examiner. Product date: Jun. 28, 2017.

* cited by examiner

*Primary Examiner* — John Kim
(74) *Attorney, Agent, or Firm* — Peter Ganjian; Patent Law Agency, LLC

(57) ABSTRACT

The present invention discloses a sterile PRP separation kit that has compartmentalized container having a cover that allows for a stage-specific exposure of sterile components of the sterile PRP separation kit housed within stage-specific compartments to a non-sterile environment commensurate with a specific stage of operation of a separation process of PRP. The sterile PRP separation kit includes a PRP tube with segregated portals for injection of blood into the PRP tube, aspiration of PRP from the PRP tube, and for maintaining an interior pressure of the PRP tube at equilibrium with ambient pressure during both injection and aspiration.

17 Claims, 36 Drawing Sheets

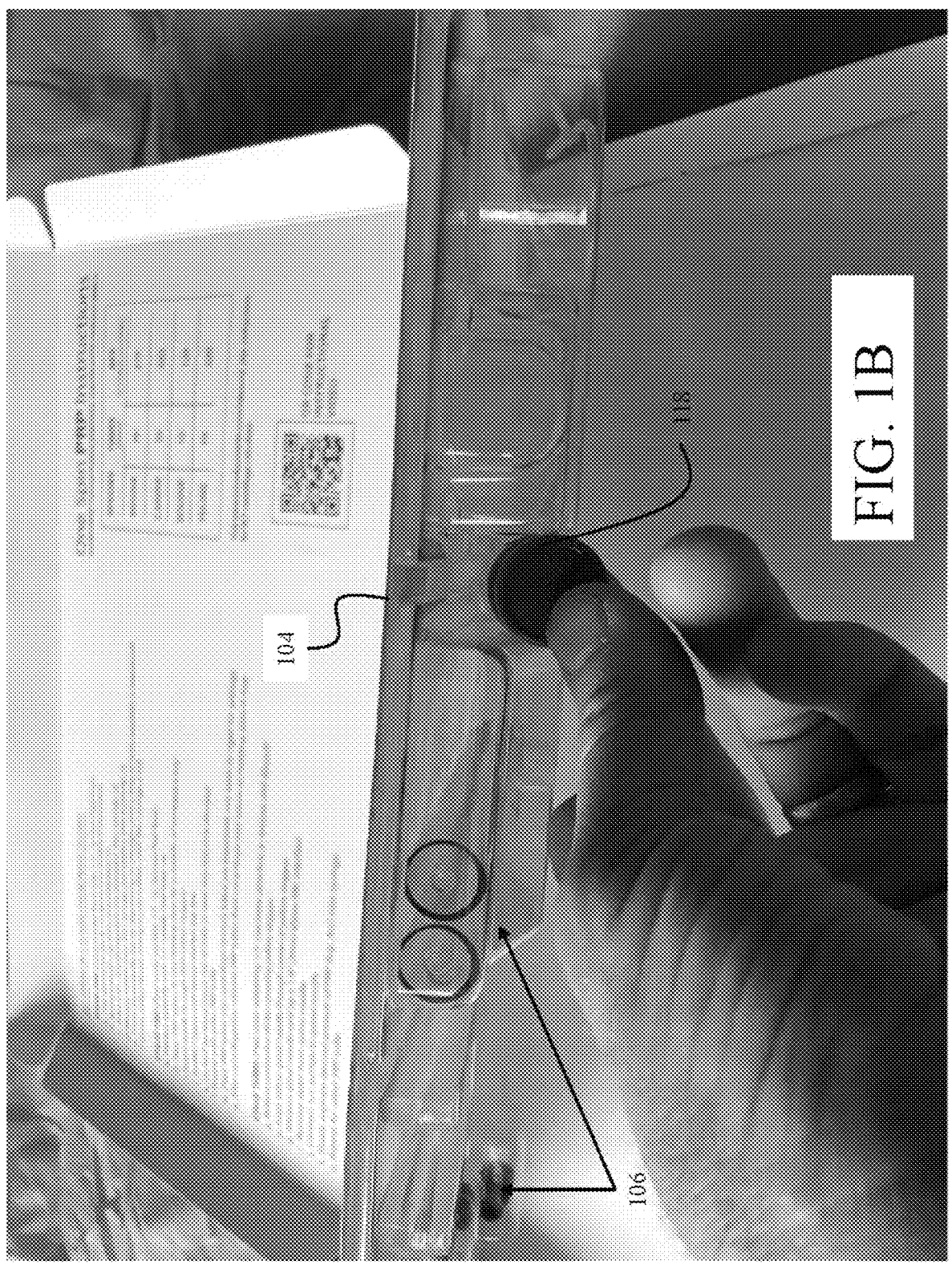

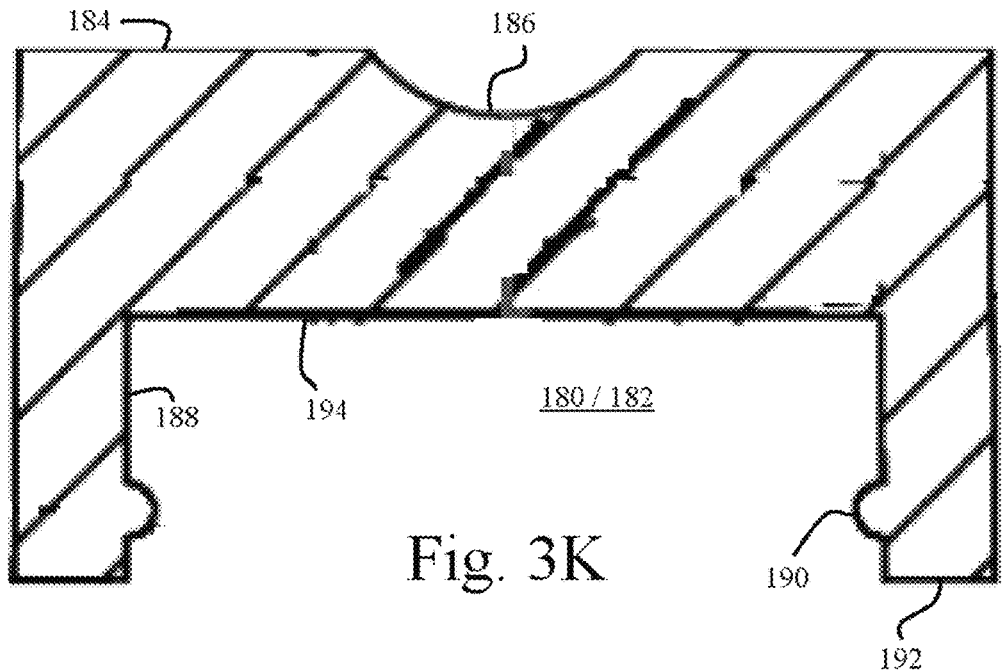
Fig. 3K
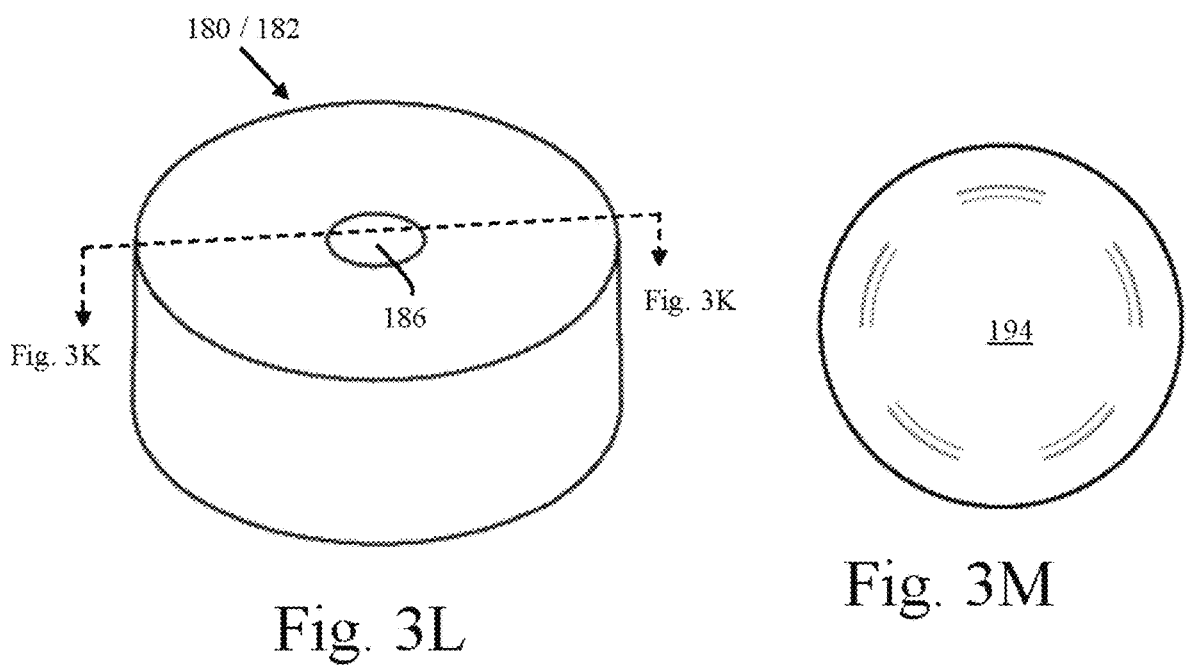
Fig. 3L
Fig. 3M

PLATELET RICH PLASMA SEPARATION KIT

CROSS-REFERENCE TO RELATED APPLICATIONS

This application claims the benefit of priority of U.S. Utility Provisional Patent Application 62/904,970, filed 24 Sep. 2019, the entire disclosure of which is expressly incorporated by reference in its entirety herein.

All documents mentioned in this specification are herein incorporated by reference to the same extent as if each individual document was specifically and individually indicated to be incorporated by reference.

It should be noted that throughout the disclosure, where a definition or use of a term in any incorporated document(s) is inconsistent or contrary to the definition of that term provided herein, the definition of that term provided herein applies and the definition of that term in the incorporated document(s) does not apply.

BACKGROUND OF THE INVENTION

Field of the Invention

One or more embodiments of the present invention relate to a platelet rich plasma separation kit.

Description of Related Art

Conventional platelet rich plasma (PRP) separation kits are well known and have been in use for a number of years. A non-limiting example of a conventional PRP separation kit is disclosed in U.S. Provisional Patent Application 62/748,093, filed 19 Oct. 2018 and assigned to ENSO DISCOVERIES, LLC, the current assignee of the present application. The entire disclosure of the U.S. Provisional Patent Application 62/748,093 is incorporated by reference in its entirety herein.

Regrettably, known conventional PRP separation kits provide improper grouping of sterile components. That is, sterile components are not grouped in accordance with a corresponding specific stage of the separation process of PRP. Accordingly, since they are grouped out of order of use in terms of separation processing stages, they may unnecessarily remain exposed to the surrounding environment longer than need be prior to their final use once their respective appropriate separation processing stage is reached. This means that the potential exists that a sterile component improperly grouped to an earlier stage of use may become contaminated.

Additionally, conventional PRP separation kits provide conventional PRP tubes with wider diameter lids that prevents the PRP tubes to properly be positioned within a centrifuge bucket. That is, the lid of a conventional PRP tube contacts and rests on outer periphery edge (or outer top ridges) of centrifuge bucket.

Unfortunately, with wider diameter lids, potential exists where the lid may be forced off of the PRP tube during centrifuge processing. This may occur because the PRP tube within centrifuge bucket is pulled due to the centrifugal force while the lid is maintained in position, pressed against the periphery edge of centrifuge bucket.

As importantly, with wider diameter lids, since centrifuge buckets are not sterile, the lid of the PRP tube contacting the periphery edge of the centrifuge bucket becomes contaminated. In fact, the entire lid is fully exposed to ambient atmosphere during centrifuge, making the lid non-sterile and potentially contaminated. This means that any contact with lid before or during aspiration of PRP by a needle may potentially contaminate the PRP sample.

A further drawback with conventional PRP tubes in general is that due to the fact that the PRP tube and the lid are separate pieces and that the lid size is larger than diameter of the PRP tube, the overall volume of conventional PRP tubes (about 5 ml) were made substantially less than (about 400% less than) the volume (about 20 ml) of a typical centrifuge bucket. Accordingly, the use of the volume of the centrifuge bucket is not maximized when using conventional PRP tubes to maximize PRP production.

Still a further drawback with conventional PRP tubes is the use of bulky butyl rubber stoppers that make the interior volume of the PRP tube airtight. That is, no air can enter or escape from the conventional PRP tube. Accordingly, once blood is collected aseptically it must be injected via a needle that pierces through the butyl rubber stopper. However, as blood is injected in to the conventional PRP tube, the interior pressure continues to increase as air within is compressed and cannot escape while more blood is continuously injected into the PRP tube. This greater interior pressure may actually damage the blood cells within the PRP tube.

It should be noted that once all blood is injected into the PRP tube, the final interior pressure of the PRP tube and that of the barrel of the syringe are at equilibrium. This equilibrium pressure is greater than outside or ambient pressure (outside of PRP tube and outside of syringe barrel). Accordingly, when the needle of the syringe is pulled out of the tube and out of the solid rubber stopper, any remaining blood within syringe barrel will be pushed out (e.g., sprayed and spilled all over) due to greater (or positive) interior pressure inside the syringe barrel.

To overcome the pressure differential between the interior syringe pressure and ambient pressure, prior to withdrawing of the syringe needle from the PRP tube, syringe plunger is pulled within syringe barrel to reduce interior pressure of both PRP tube and syringe barrel to a negative pressure (compared to outside or ambient pressure). Accordingly, when syringe needle is finally fully pulled out no content within syringe barrel is pushed out due to any positive pressure within syringe barrel. These steps prevent blood spillage.

The opposite of the above steps must be carried out when extracting PRP from the conventional PRP tubes. That is, as is well-known, prior to aspiration of PRP, air is injected into the PRP tube to create a positive pressure within PRP tube to enable aspiration of PRP. Thereafter, the generated force of the positive pressure within PRP tube will force the PRP into the syringe barrel.

If no positive pressure is created in the PRP tube prior to aspiration thereof, when extracting PRP, negative pressure will be generated in the PRP tube, which would impede aspiration of the PRP.

The amount of air injected into the PRP tube to generate the positive pressure for extraction of PRP may be determined by the amount of PRP desired to be aspirated. For example, for aspiration of 1.5 cc of PRP, the plunger of the syringe is drawn up to 1.5 cc of air (1.5 cc is marked on the syringe barrel). Thereafter, the 1.5 cc of air within the syringe barrel is injected into the PRP tube to generate the positive pressure for aspiration of PRP. Further adjustments of the plunger may be required if more or less PRP is needed.

It should be noted that the conventional butyl rubber stoppers are more rigid or stiff (about 80 shore-hardness and 5 mm thick) and hence, spinal needles used to extract PRP from already centrifuged PRP tubes would bend when inserting them through the solid rubber stoppers. The problem with butyl rubber material is that its rigidity or stiffness is increased in colder environments.

Accordingly, in light of the current state of the art and the drawbacks to current platelet rich plasma separation kits mentioned above, a need exists for a platelet rich plasma separation kit that would overcome all of the above-mentioned drawbacks.

BRIEF SUMMARY OF THE INVENTION

A non-limiting, exemplary aspect of an embodiment of the present invention provides a sterile platelet rich plasma (PRP) separation kit, comprising:
a compartmentalized container having a cover that allows for a stage-specific exposure of sterile components of the sterile PRP separation kit housed within stage-specific compartments to a non-sterile environment commensurate with a specific stage of operation of a separation process of PRP, having:
a first stage that includes a first set of sterile components housed within a first set of compartments and exposed only for aseptic collection of blood;
with the first set of sterile components, comprising:
a first stage syringe;
a first stage needle; and
a winged infusion set;
a second stage that includes a second set of sterile components housed within a second set of compartments and exposed only for filling in a PRP tube with aseptically collected blood from the first stage;
with the second set of sterile components, comprising:
the PRP tube; and
a second stage needle that is connected to the first stage syringe for injecting the aseptically collected blood into the PRP tube for separation of PRP;
a third stage that includes a third set of sterile components housed within a third set of compartments and exposed only for aspirating the PRP from the PRP tubes of the second stage;
with the third set of sterile components, comprising:
a lateral aspiration spinal needle;
a third stage syringe with a third stage needle; and
a syringe cap.

Another non-limiting, exemplary aspect of an embodiment of the present invention provides a sterile platelet rich plasma (PRP) separation kit, comprising:
a compartmentalized container having a cover that allows for a stage-specific exposure of sterile components of the sterile PRP separation kit housed within stage-specific compartments to a non-sterile environment commensurate with a specific stage of operation of a separation process of PRP, having:
a first stage for aseptic collection of blood;
a second stage for separation of PRP within a PRP tube; and
a third stage for aspirating the PRP from the PRP tube of the second stage;
wherein:
the PRP tube is comprised of:
the segregated openings that includes:
a first opening for injection of blood into the PRP tube;
a second opening for aspiration of PRP from the PRP tube; and
a third opening for maintaining an interior pressure of the PRP tube at equilibrium with ambient pressure.

Yet another non-limiting, exemplary aspect of an embodiment of the present invention provides a sterile platelet rich plasma (PRP) separation kit, comprising:
a cover that encloses a container;
the cover includes indicia for instructing stage-based opening of the cover commensurate with a specific stage of operation of a separation process of platelet rich plasma to enable access to a set of sterile components for the specific stage;
the sterile components are arranged within one or more compartments of the container, and grouped in accordance with a corresponding specific stage of the separation process of platelet rich plasma.

These and other features and aspects of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" may be used to mean "serving as an example, instance, or illustration," but the absence of the term "exemplary" does not denote a limiting embodiment. Any embodiment described as "exemplary" is not necessarily to be construed as preferred or advantageous over other embodiments. In the drawings, like reference character(s) present corresponding part(s) throughout.

DETAILED DESCRIPTION OF THE INVENTION

Figure 1A:
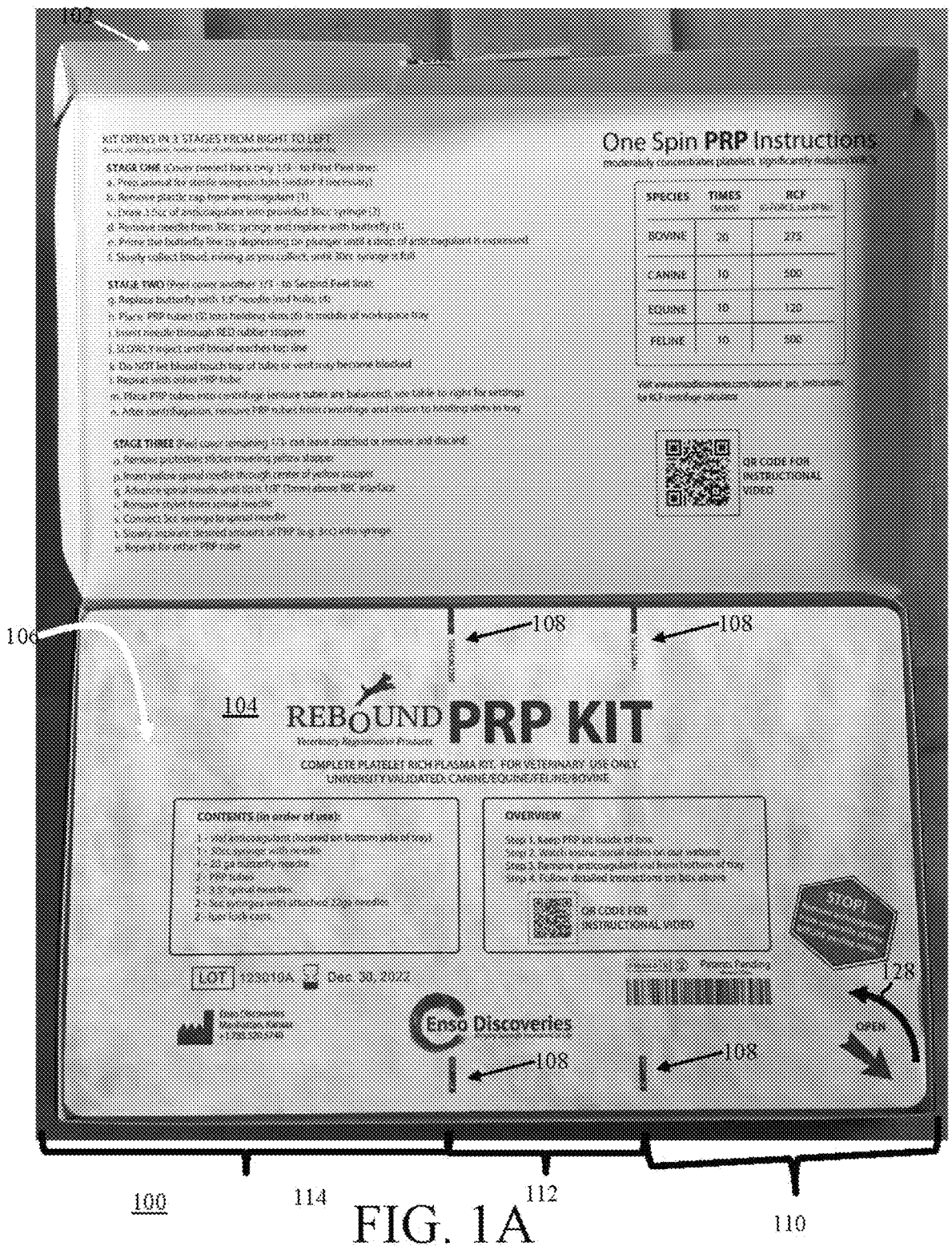
FIGS. 1A to 1C are non-limiting, exemplary illustrations of a platelet rich plasma separation kit in accordance with one or more embodiments of the present invention.

The detailed description set forth below in connection with the appended drawings is intended as a description of presently preferred embodiments of the invention and is not intended to represent the only forms in which the present invention may be constructed and or utilized.

It is to be appreciated that certain features of the invention, which are, for clarity, described in the context of separate embodiments, may also be provided in combination in a single embodiment. Conversely, various features of the invention that are, for brevity, described in the context of a single embodiment may also be provided separately or in any suitable sub-combination or as suitable in any other described embodiment of the invention. Stated otherwise, although the invention is described below in terms of various exemplary embodiments and implementations, it should be understood that the various features and aspects described in one or more of the individual embodiments are not limited in their applicability to the particular embodiment with which they are described, but instead can be applied, alone or in various combinations, to one or more of the other embodiments of the invention.

One or more embodiments of the present invention provide a platelet rich plasma separation kit that provides a stage-specific exposure of sterile components of the sterile platelet rich plasma separation kit to a non-sterile environment exactly commensurate with a specific stage of a separation process of platelet rich plasma. Critically and advantageously, since components are grouped in the order of use in terms of separation processing stages, they will not be exposed to the surrounding prior to their final use once their respective appropriate separation processing stage is reached. This means that the sterile component will not become contaminated prior to their use.

One or more embodiments of the present invention provide a platelet rich plasma separation kit that provides a PRP tube without the need or requirement for a lid, while maintaining segregated openings for injection of blood and extraction of RPP. Critically and advantageously, since there is no lid, there is no contamination of lid and as importantly, no possible contamination of a needle that may contact a contaminated lid before or during aspiration of PRP.

One or more embodiments of the present invention provide a platelet rich plasma separation kit that provides a PRP tube with larger volume to maximize the use of the volume of countertop centrifuge bucket. This maximizes the volume of PRP processed using a countertop centrifuge. Critically and advantageously, this enables production of a larger volume of PRP due to larger sized PRP tubes when using countertop centrifuge, accordingly, there is no requirement or a need for a larger, more expensive centrifuge.

One or more embodiments of the present invention provide a platelet rich plasma separation kit that provides a PRP tube without the use of solid rigid rubber stoppers. Critically and advantageously, this prevents spinal needles from bending.

One or more embodiments of the present invention provide a platelet rich plasma separation kit that obviates the need to manually (or actively) vary the internal pressures of the PRP tube and or the syringe barrel for mere injection or extraction of fluids. Instead, one or more embodiments of the present invention provide a platelet rich plasma separation kit that passively (or automatically) maintain in the equilibrium an interior pressure of PRP tube with exterior (ambient) pressure during injection of blood into and/or extraction of PRP from the PRP tube. Critically and advantageously, this "passive" process prevents blood spillage, damage to blood cells, and reduces the steps detailed above (and hence the time) required to inject blood and or extract PRP.

Figure 1C:
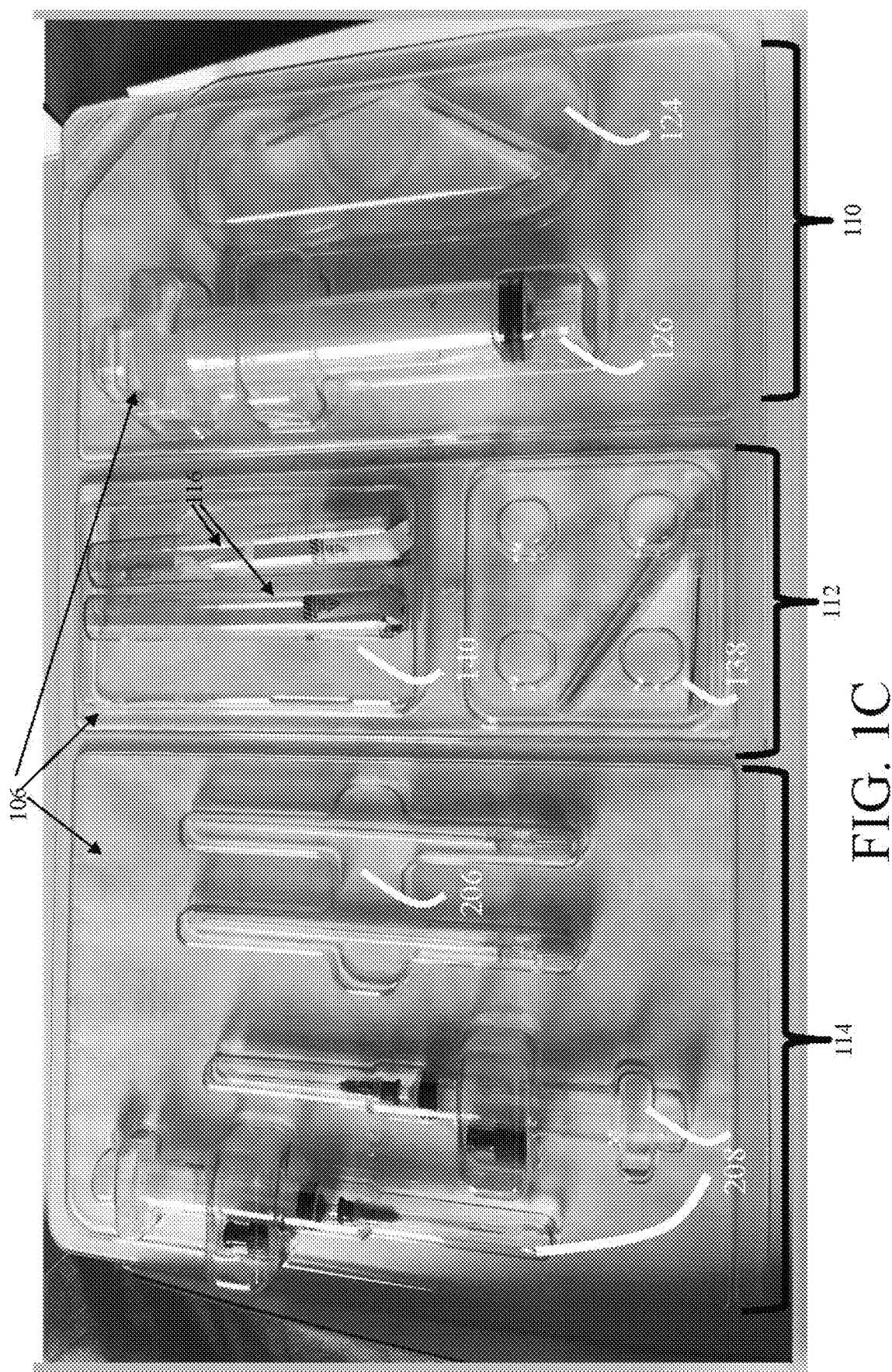

FIGS. 1A to 1C are non-limiting, exemplary illustrations of a platelet rich plasma separation kit in accordance with one or more embodiments of the present invention. As illustrated in FIGS. 1A to 1C, one or more embodiments of the present invention provide a sterile platelet rich plasma separation kit 100 comprised of a box 102 that includes a plastic container or tray 106 with a Tyvek cover 104. Cover 104 encloses container 106 with plurality of compartments 114. FIG. 1A shows cover 104 of tray 106 whereas FIGS. 1B and 1C show (the flipped or back transparent side) of tray 106.

Sterile platelet rich plasma separation kit 100 allows for a stage-specific 110, 112, 114 exposure of sterile components (detailed below) of the sterile platelet rich plasm separation kit 100 to a non-sterile environment commensurate with a specific stage of operation of a separation process of platelet rich plasma.

As best shown in FIG. 1A, cover 104 encloses container (or tray) 106 that holds sterile components. Cover 104 includes indicia 108 for instructing stage-based opening of cover 104 commensurate with a specific stage 110, 112, and 114 of operation of a separation process of platelet rich plasma to enable access to a set of sterile components for the specific stage 110, 112, and 114. The sterile components are used in separation process of platelet rich plasma, which are further detailed below.

As best shown in FIG. 1C and further detailed below, the sterile components are arranged within one or more compartments of container 106 and grouped in accordance with a corresponding specific stage 110, 112, and 114 of the separation process of platelet rich plasma. It should be noted that the position and orientation of each compartment within a specific stage may be varied. Further, the position and orientation of components within their respective compartment may be varied. However, the sterile components must be grouped and arranged within one or more compartments corresponding to the specific stage of the separation process of PRP.

Cover 104 allows for a stage-specific exposure (for example, three stages 110, 112, and 114) of the sterile components of the sterile PRP separation kit to a non-sterile environment commensurate with a specific stage of a separation process of PRP.

The three stages of sterile PRP separation include a first stage 110 for aseptic collection of blood, a second stage 112 for filling PRP tubes 116 with blood followed by separation of PRP (e.g., using density gradient centrifugation), and a third stage 114 for aspiration of PRP.

As best shown in FIG. 1B, the sterile platelet rich plasma separation kit 100 may optionally include an anticoagulant 118, in some instances taped to the outside of tray (or container) 106, outside of the sterile environment. Use of anticoagulant 118 in PRP separations are well known. (FIG. 1C shows tray 106 with anticoagulant 108 removed.)

Figure 2A:
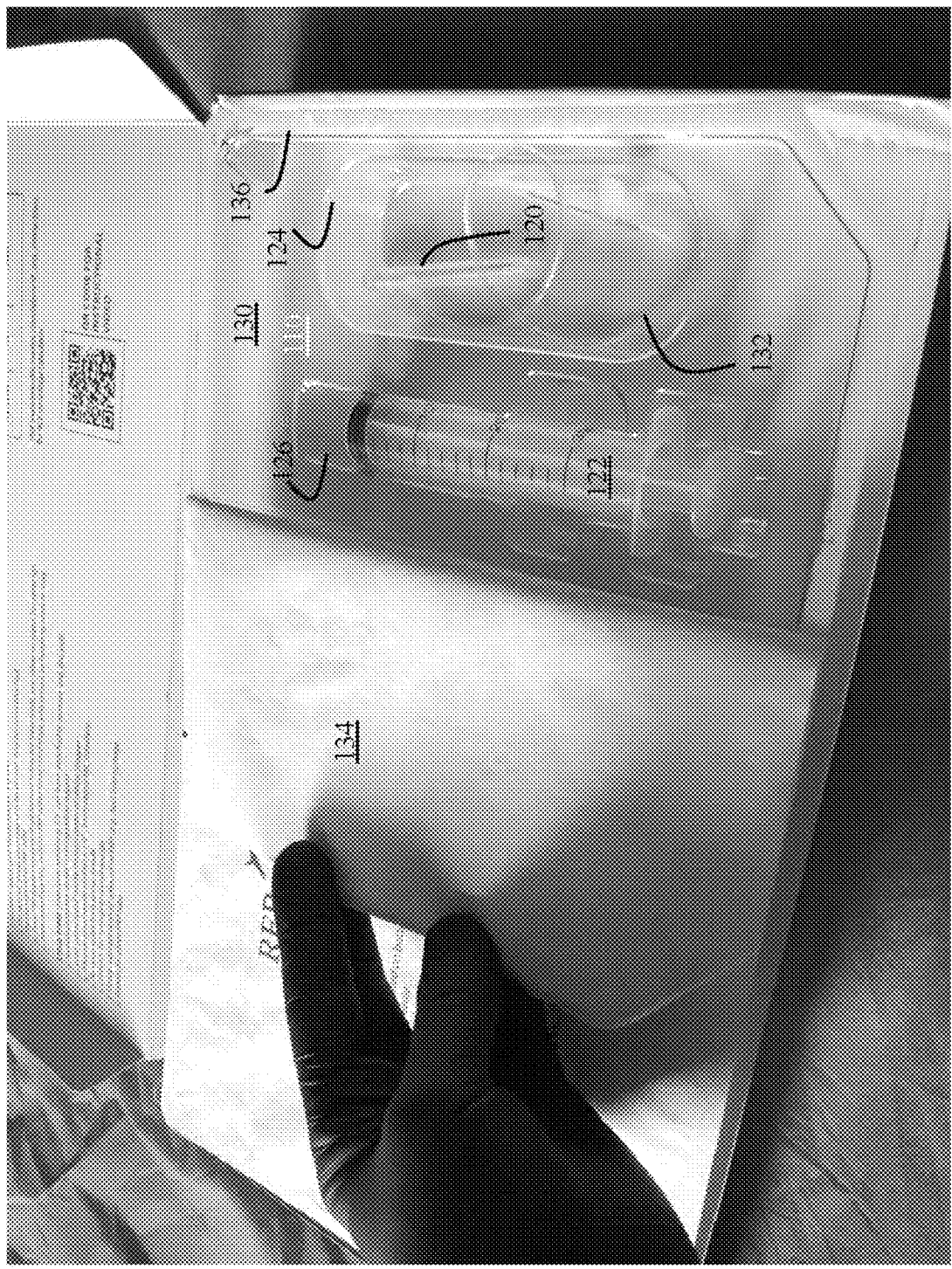
FIGS. 2A to 2C are non-limiting, exemplary illustrations of a first stage of the platelet rich plasma separation kit for aseptic collection of blood in accordance with one or more embodiments of the present invention.
Figure 2B:
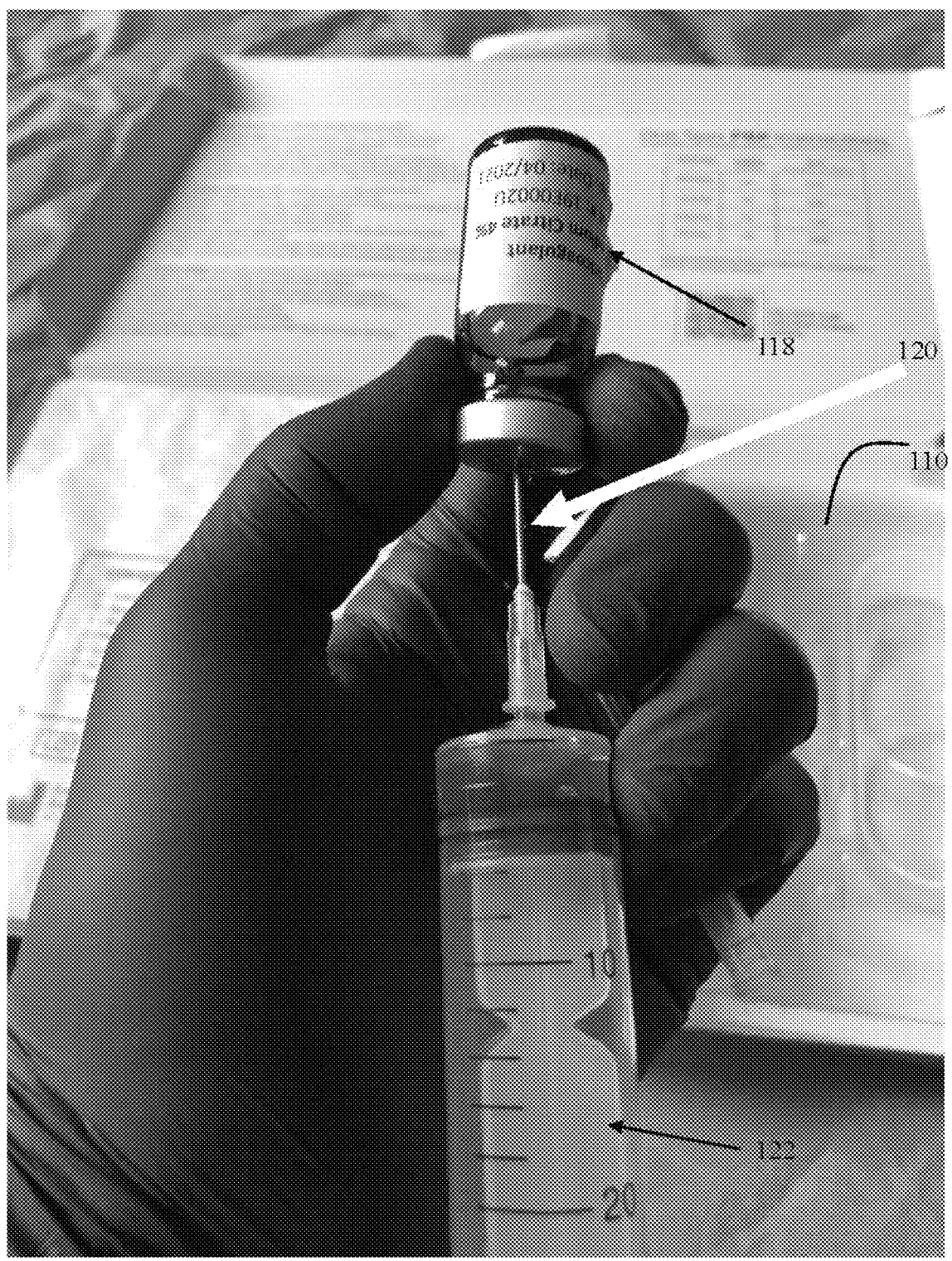
Figure 2C:
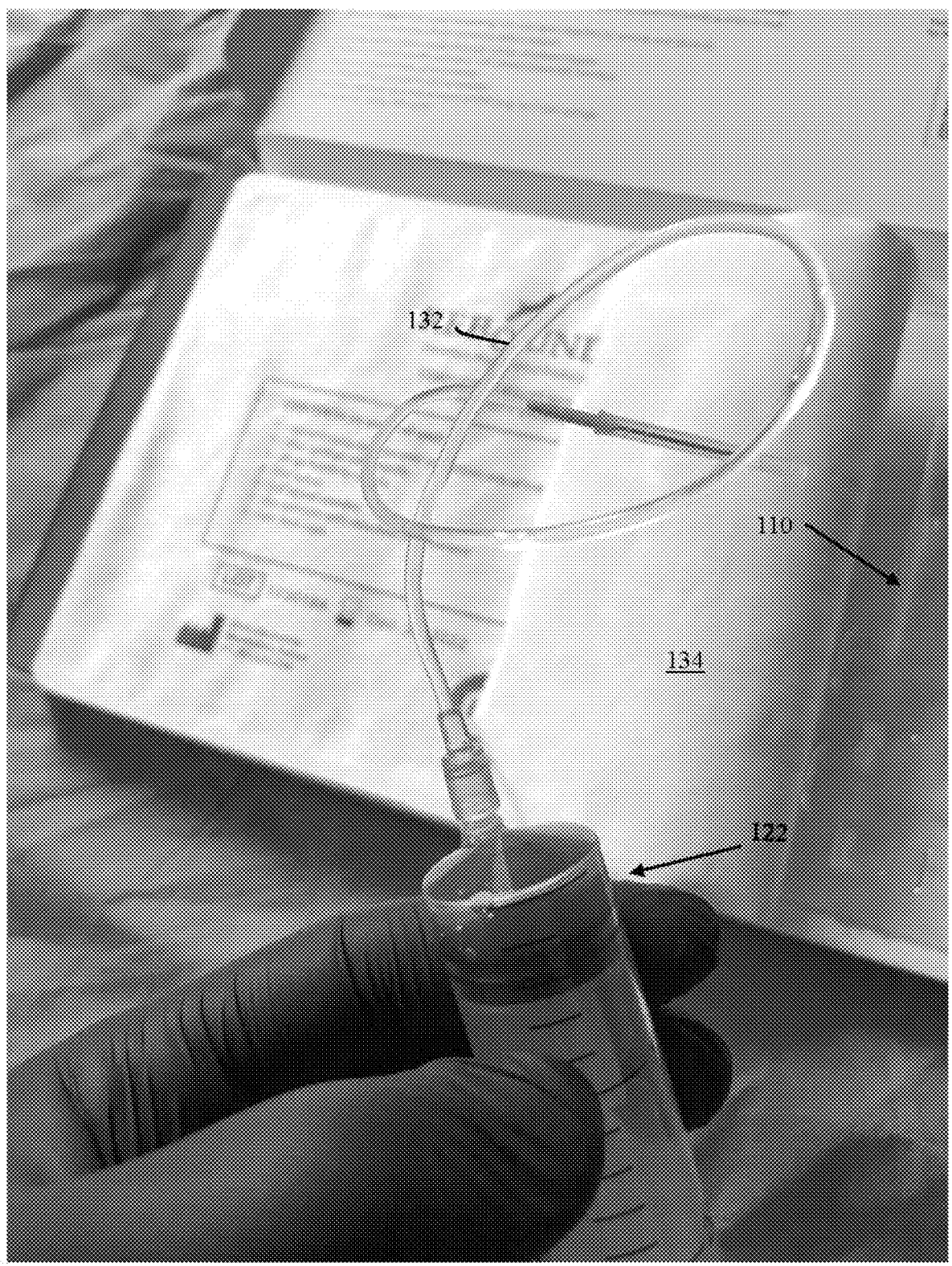

FIGS. 2A to 2C are non-limiting, exemplary illustrations of a first stage of the platelet rich plasma separation kit for aseptic collection of blood in accordance with one or more embodiments of the present invention. As illustrated, first stage 110 that includes a first set of sterile components (detailed below) housed within a first set of compartments 124 and 126 and exposed only for aseptic collection of blood.

Cover 104 may be peeled away as shown by arrow 128 (FIG. 1A) from the right bottom corner of cover 104 with indicia "OPEN" to expose first stage 110 and its compartmentalized sterile components. Container 106 includes stage separation walls 130 that separate stages 110, 112, and 114.

A top surface of the stage separation walls 130 includes an adhesive that maintains an underside 134 (FIG. 2A) of cover 104 attached to top surface 136 of stage separation wall 130. This would mean that an extra amount of force would be required to peel off cover 104 further into a next stage. This way, a next stage is prevented from being accessed "accidentally," but would require an intentional application of force. Accordingly, users must intentionally apply and exert extra force to pull cover 104 and overcome the adhesive force to peel it off to expose the next stage. Therefore, only those compartments and their respective components are exposed at any given time that are to be used for a specific stage of PRP separation.

As illustrated in FIGS. 2A to 2C, first set of sterile components of first stage 110 include a first syringe (plunger and barrel) 122 in compartment 126. In this non-limiting, exemplary instance, first syringe 122 may comprise of a 30 cc syringe needle. A larger first stage syringe 122 of 30 cc is used due to the use of larger PRP tube 116 of about 15 ml (detailed below). Conventional kits (for a countertop centrifuge) have a smaller sized syringe of about 20 cc and use smaller PRP tubes of about 5 ml, resulting in generated PRP amounts three times less than the present invention.

As further illustrated, first stage 110 further includes at least one first stage needle 120, including a winged infusion set (e.g., a butterfly needle) 132 of about 20 ga (gauge) positioned in compartment 124. Aseptic collection of blood is well known and conventional. As illustrated in FIGS. 2B and 2C, optionally, anticoagulant 118 may be aspirated and used in a well-known conventional manner using the components of first stage 110 of the present invention prior to aseptic aspiration of blood from a subject.

Figure 3A:
FIGS. 3A to 3S are non-limiting, exemplary illustrations of a second stage of the platelet rich plasma separation kit for filling PRP tubes with blood followed by separation of PRP (e.g., using density gradient centrifugation) in accordance with one or more embodiments of the present invention.
Figure 3B:
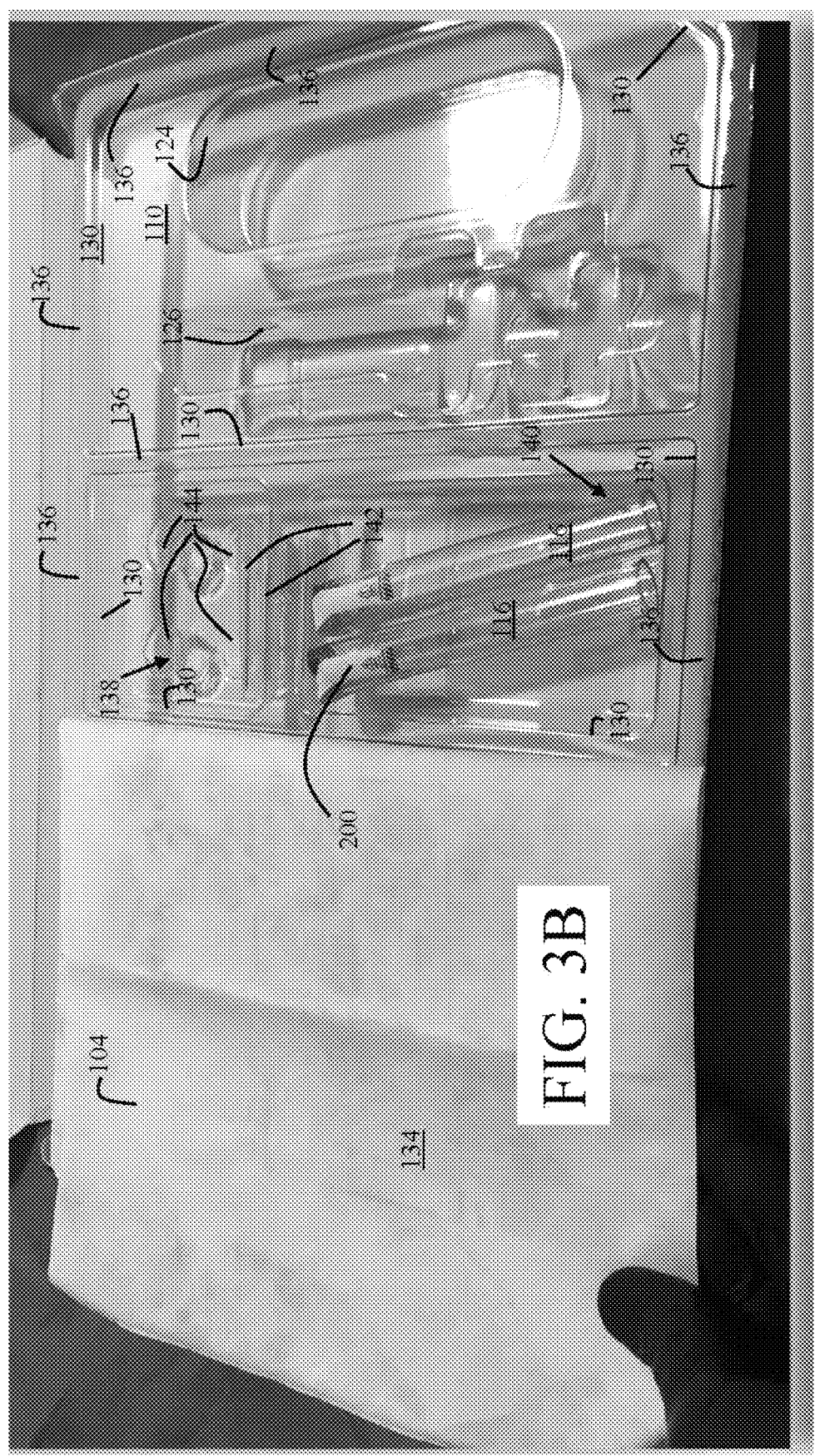
Figure 3C:
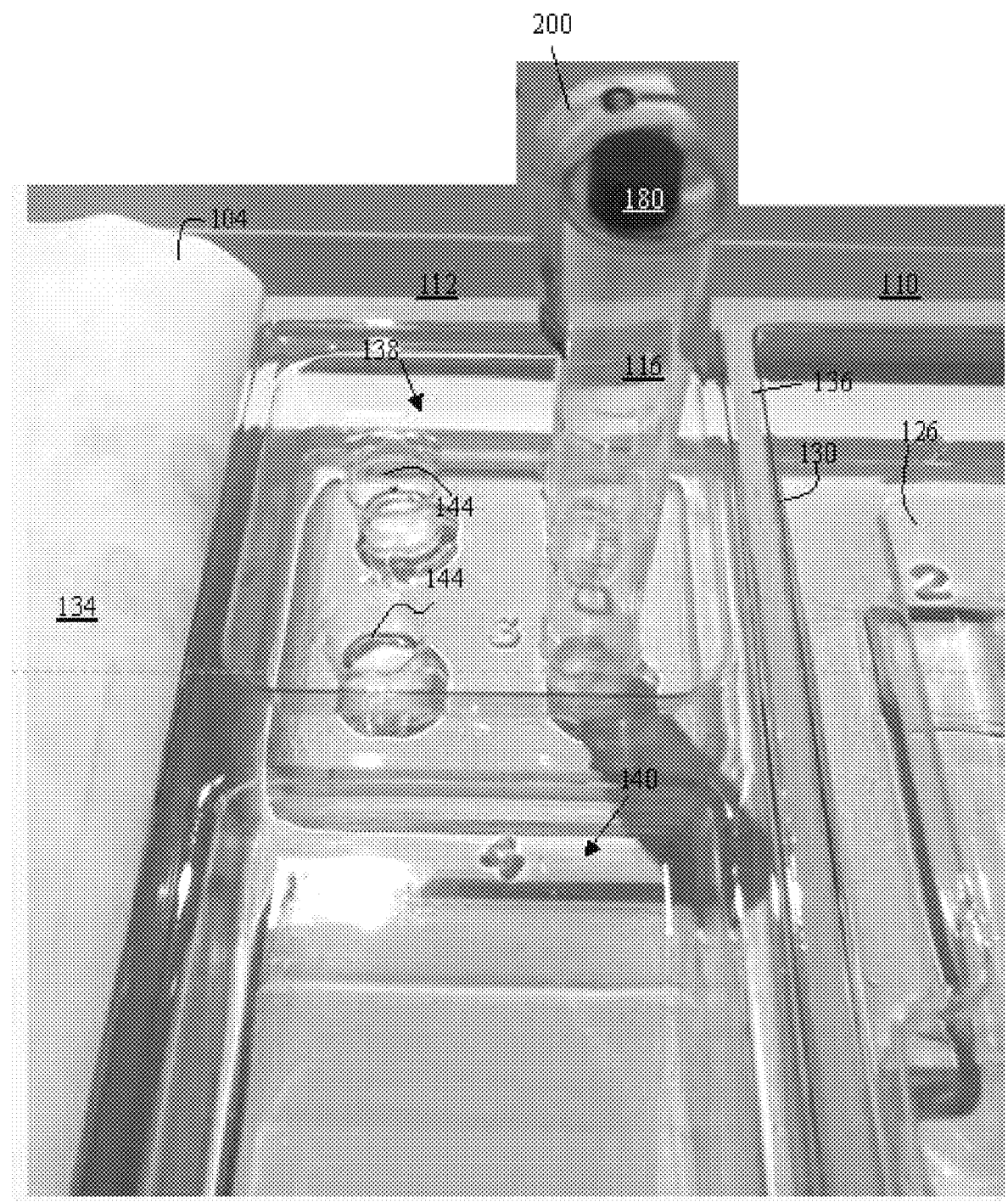
Figure 3D:
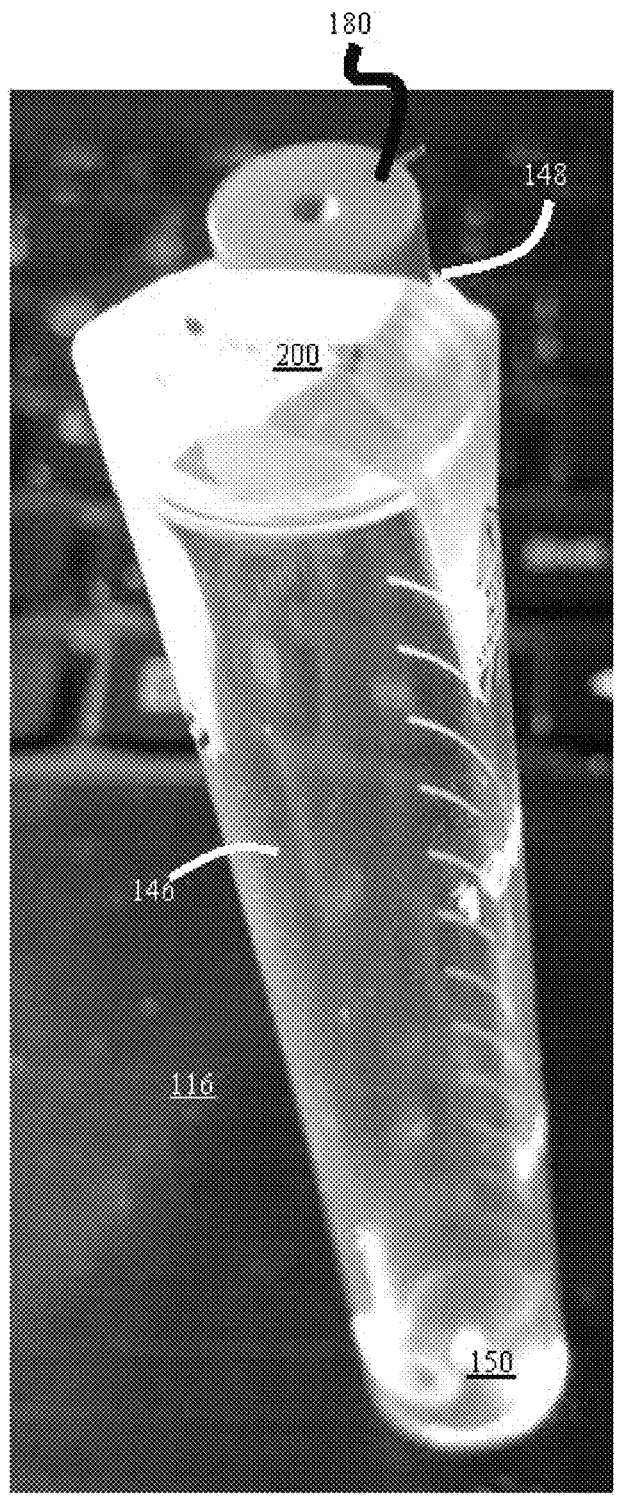
Figure 3E:
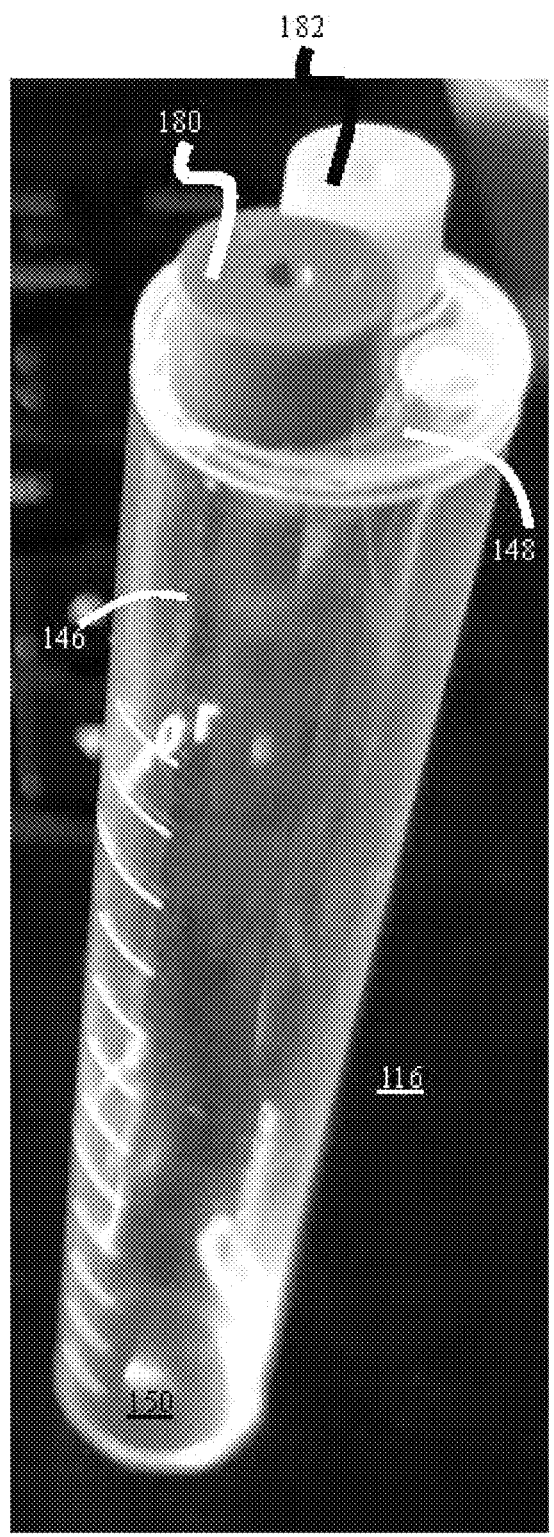
Figure 3F:
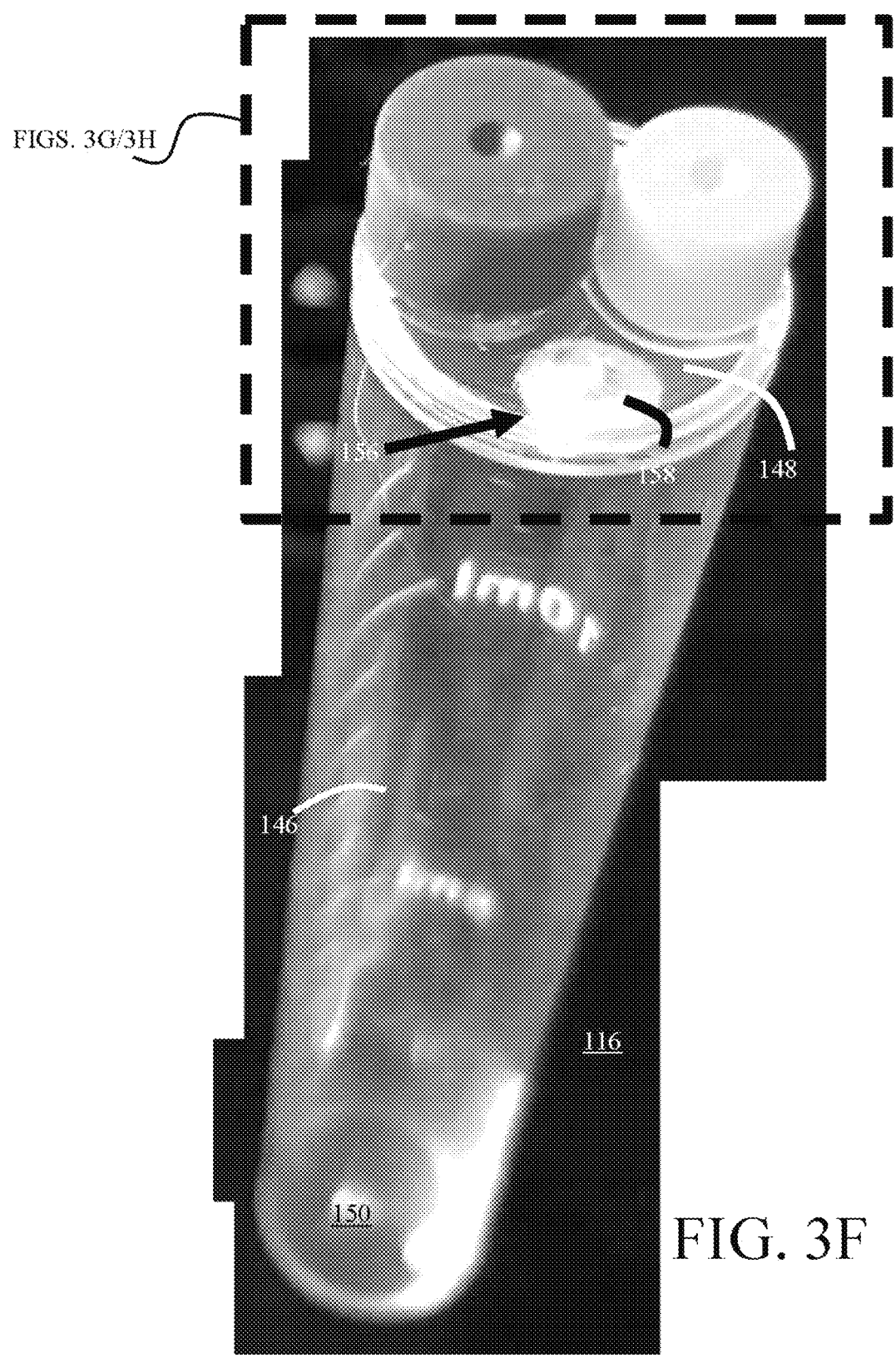
Figure 3G:
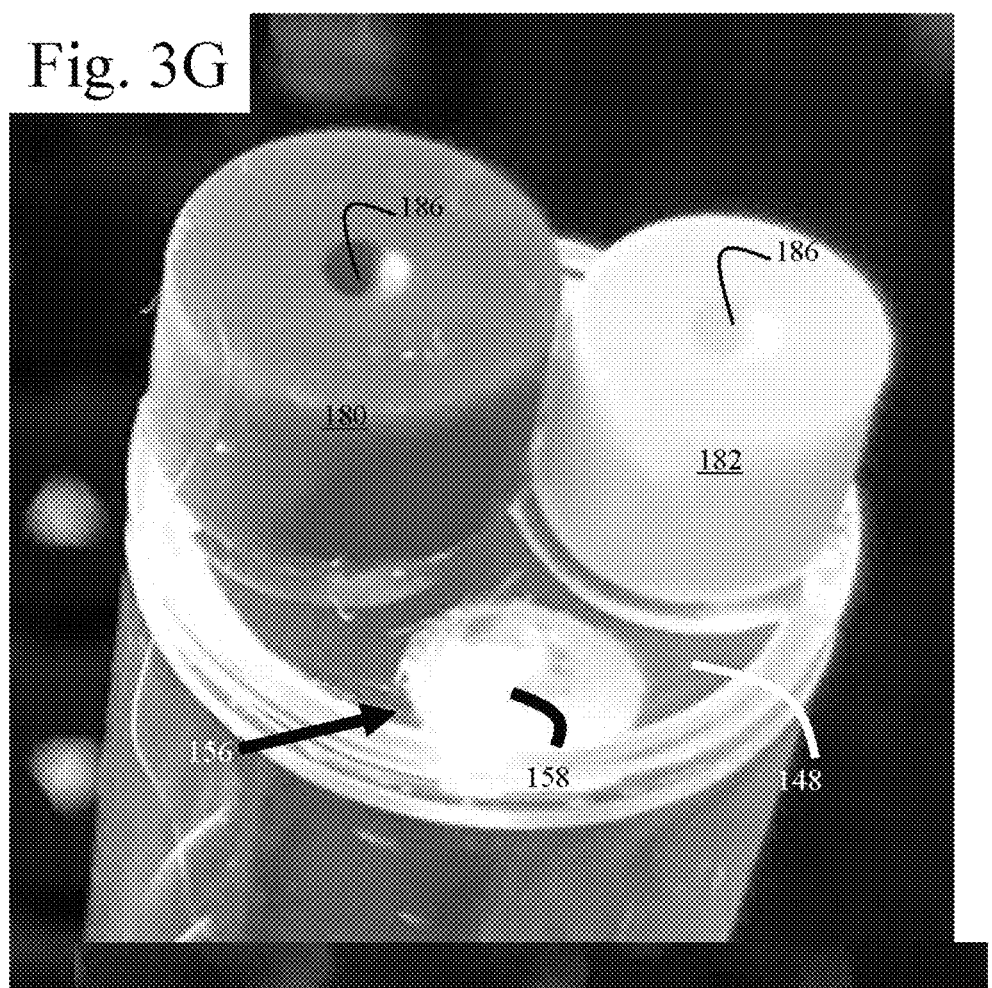
Figure 3H:
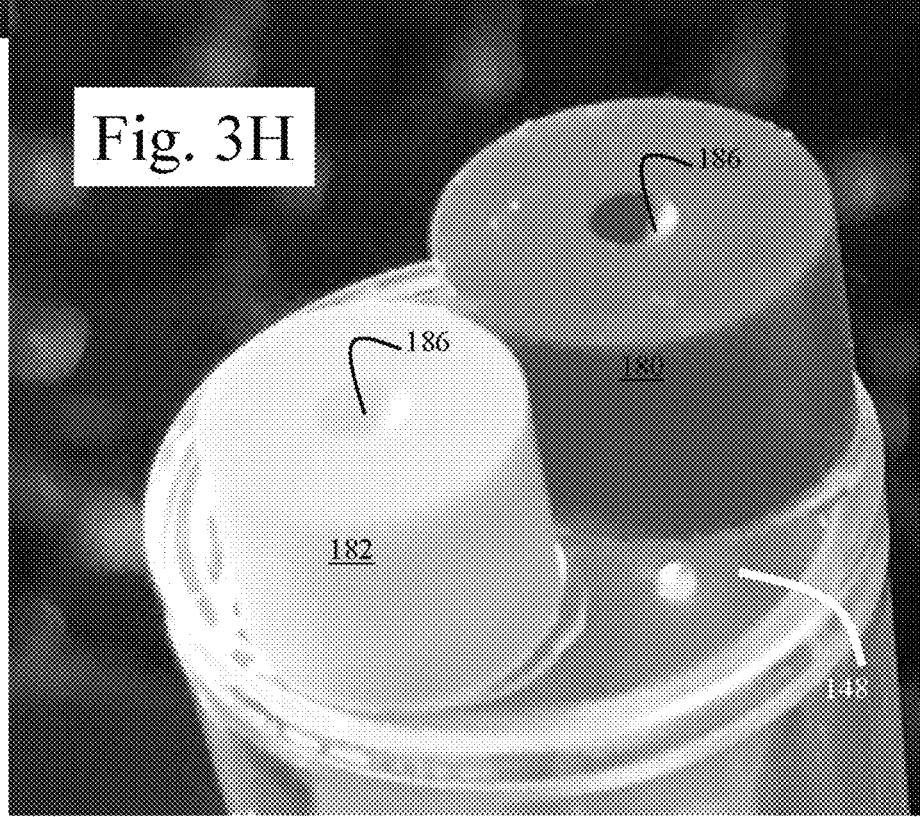
Figure 3I:
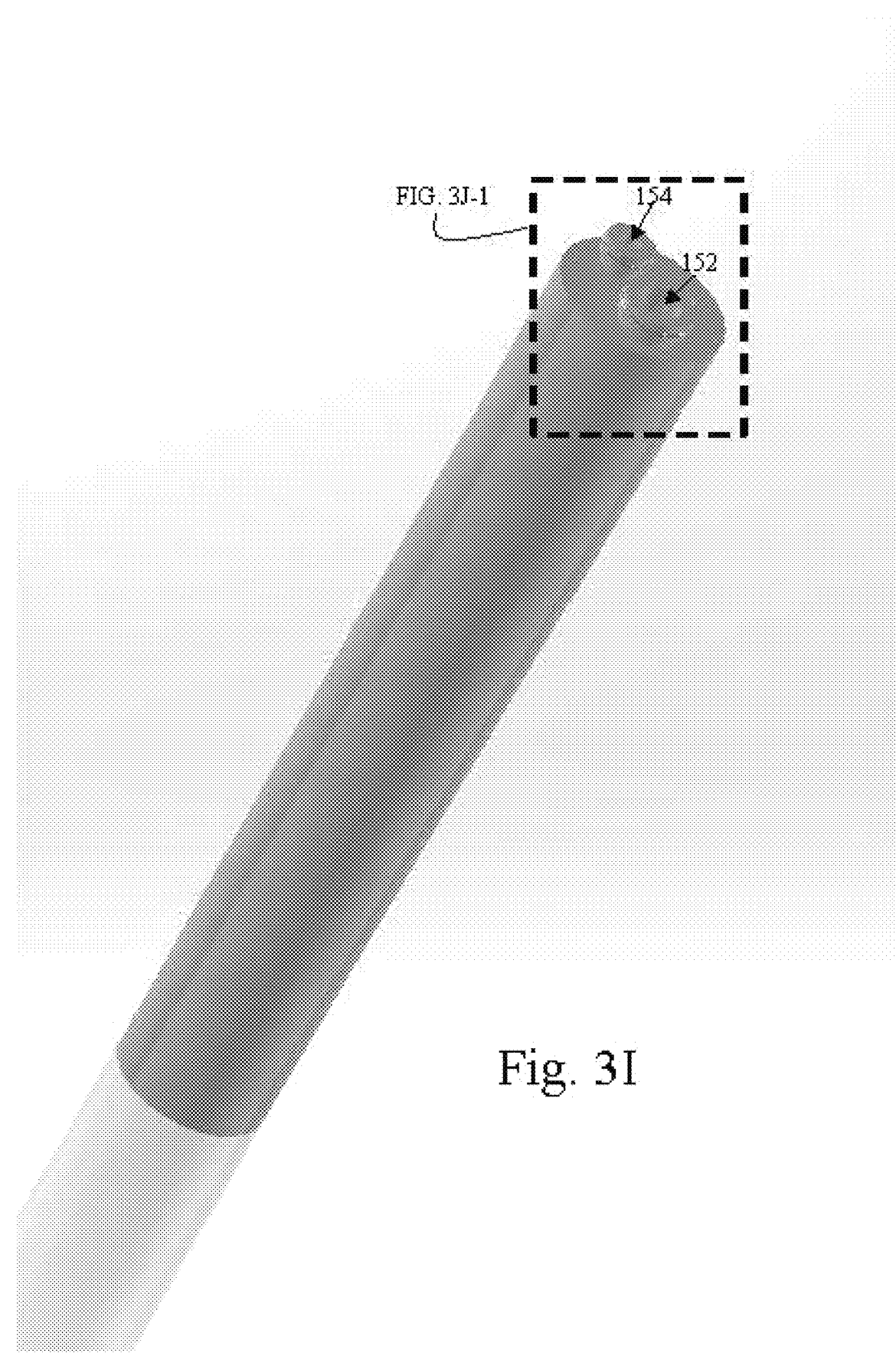
Figures 1, 3J:
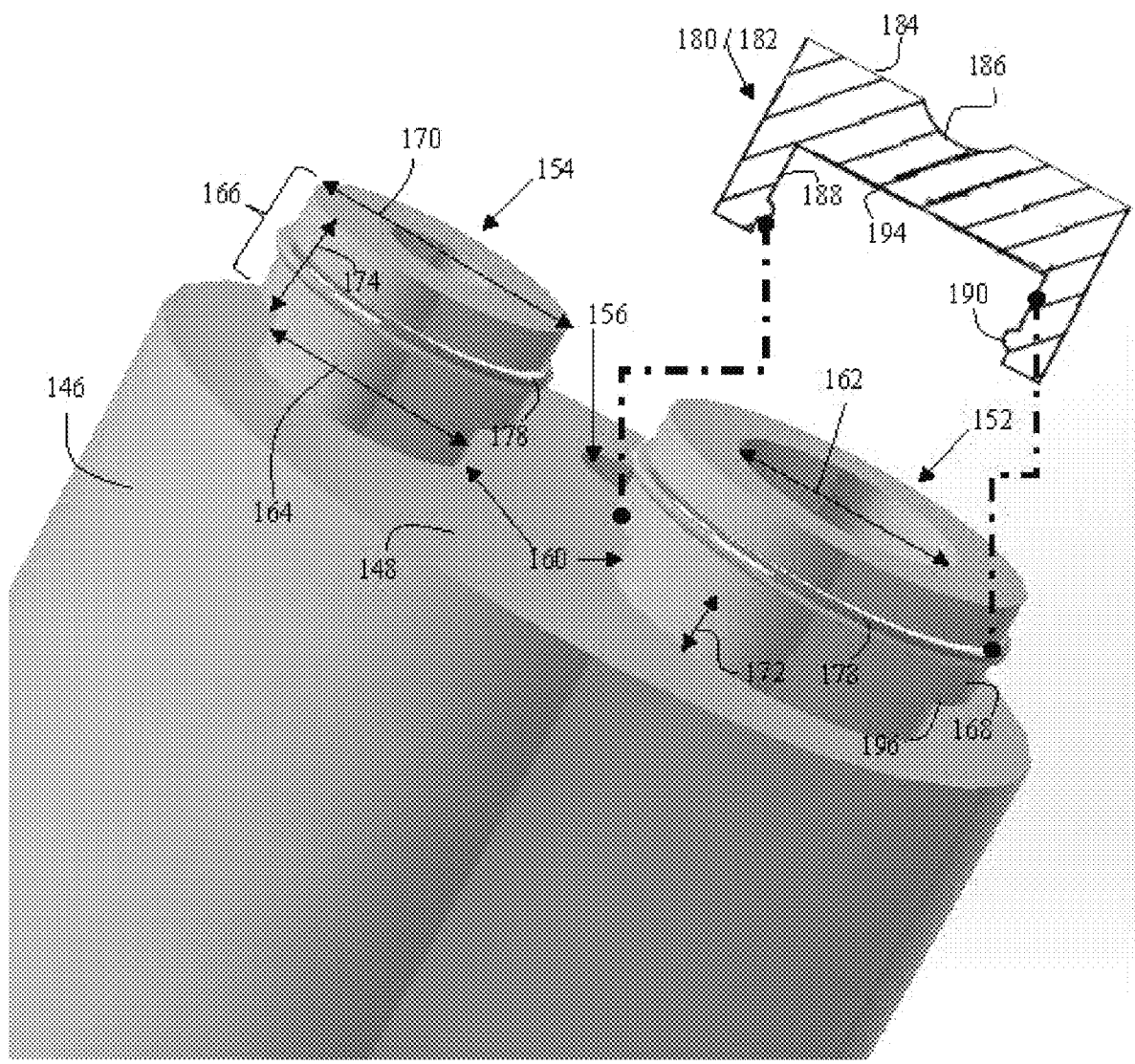
Figures 2, 3J:
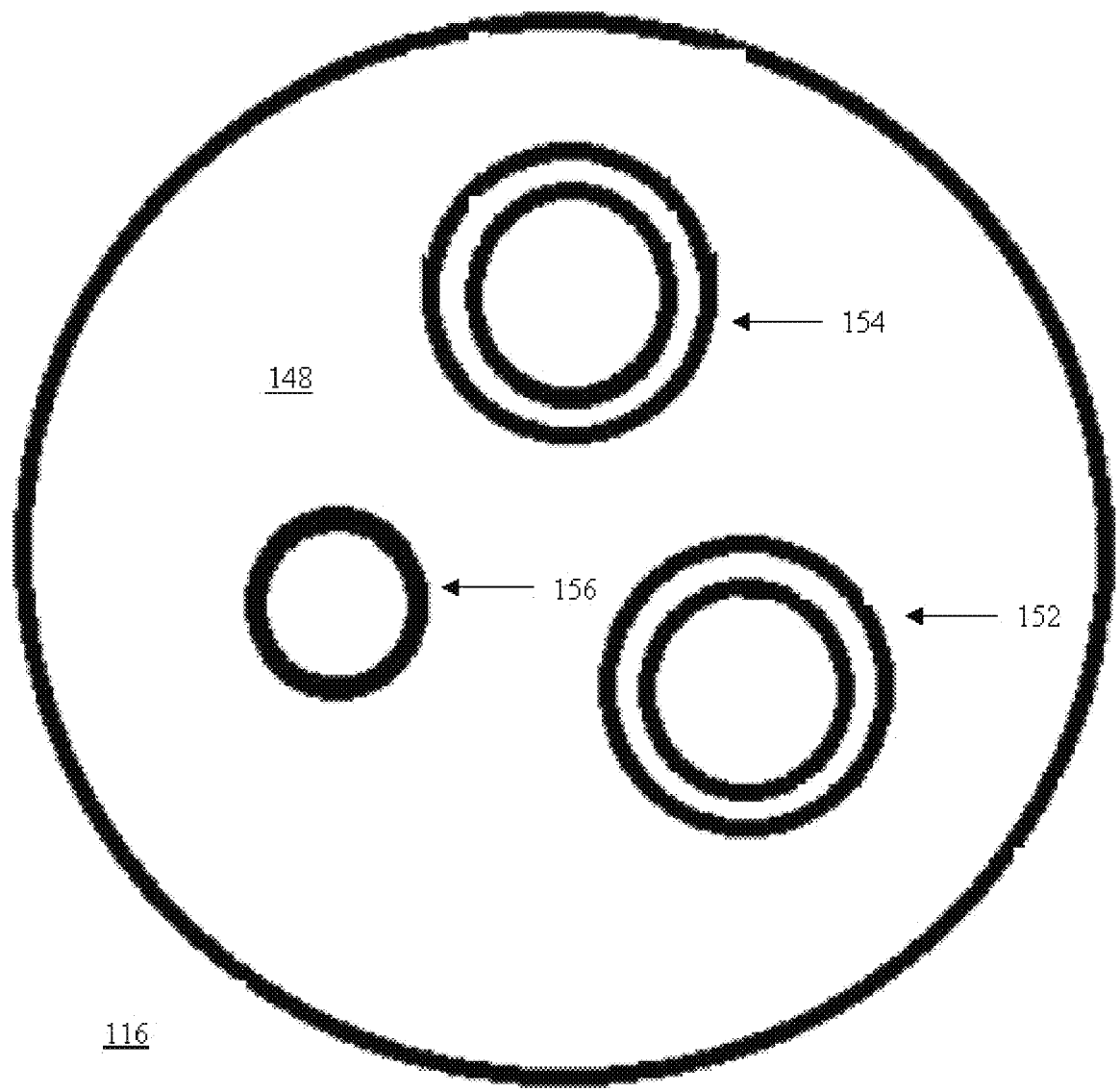
Figure 3N:
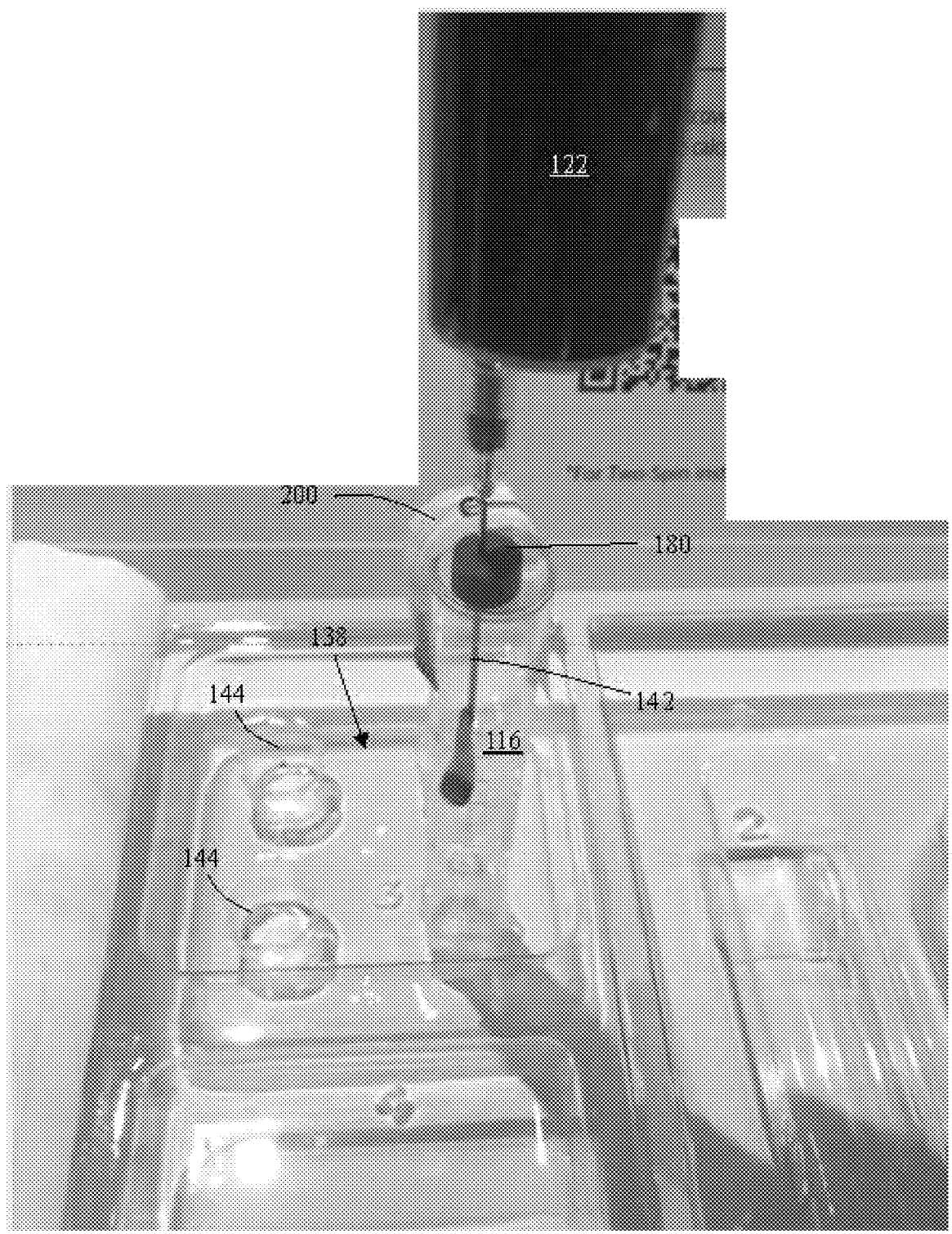
Figure 3O:
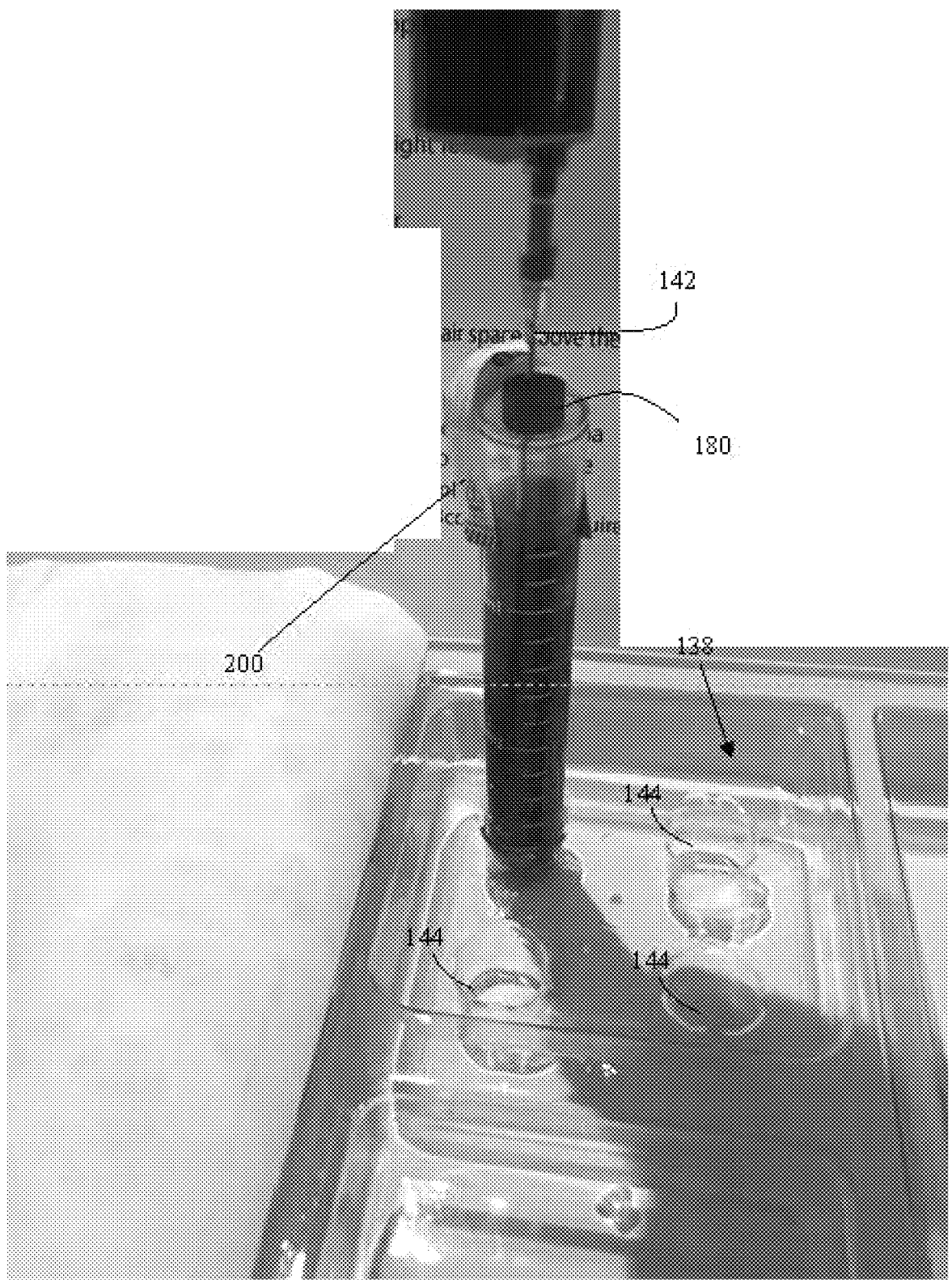
Figure 3P:
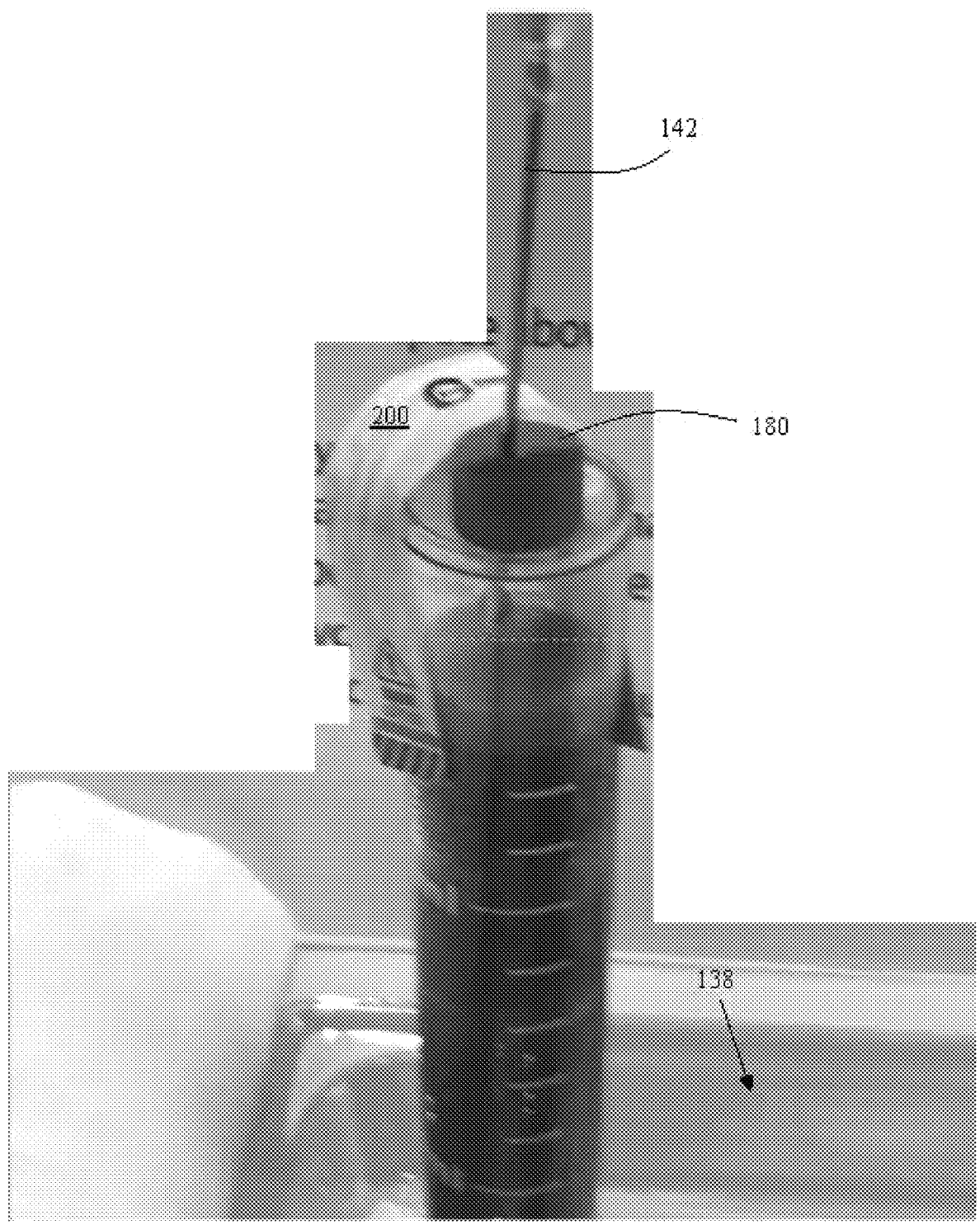
Figure 3Q:
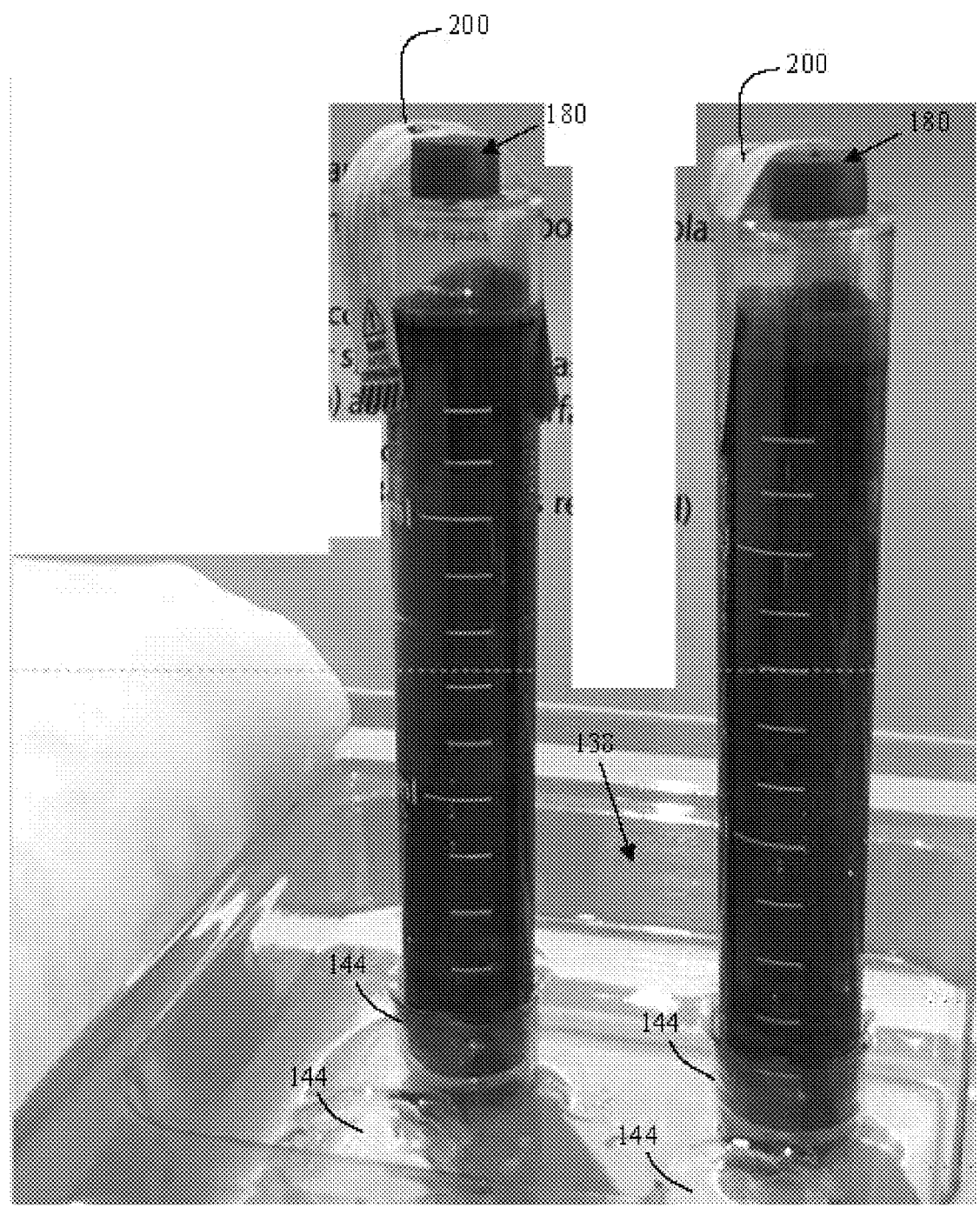
Figure 3R:
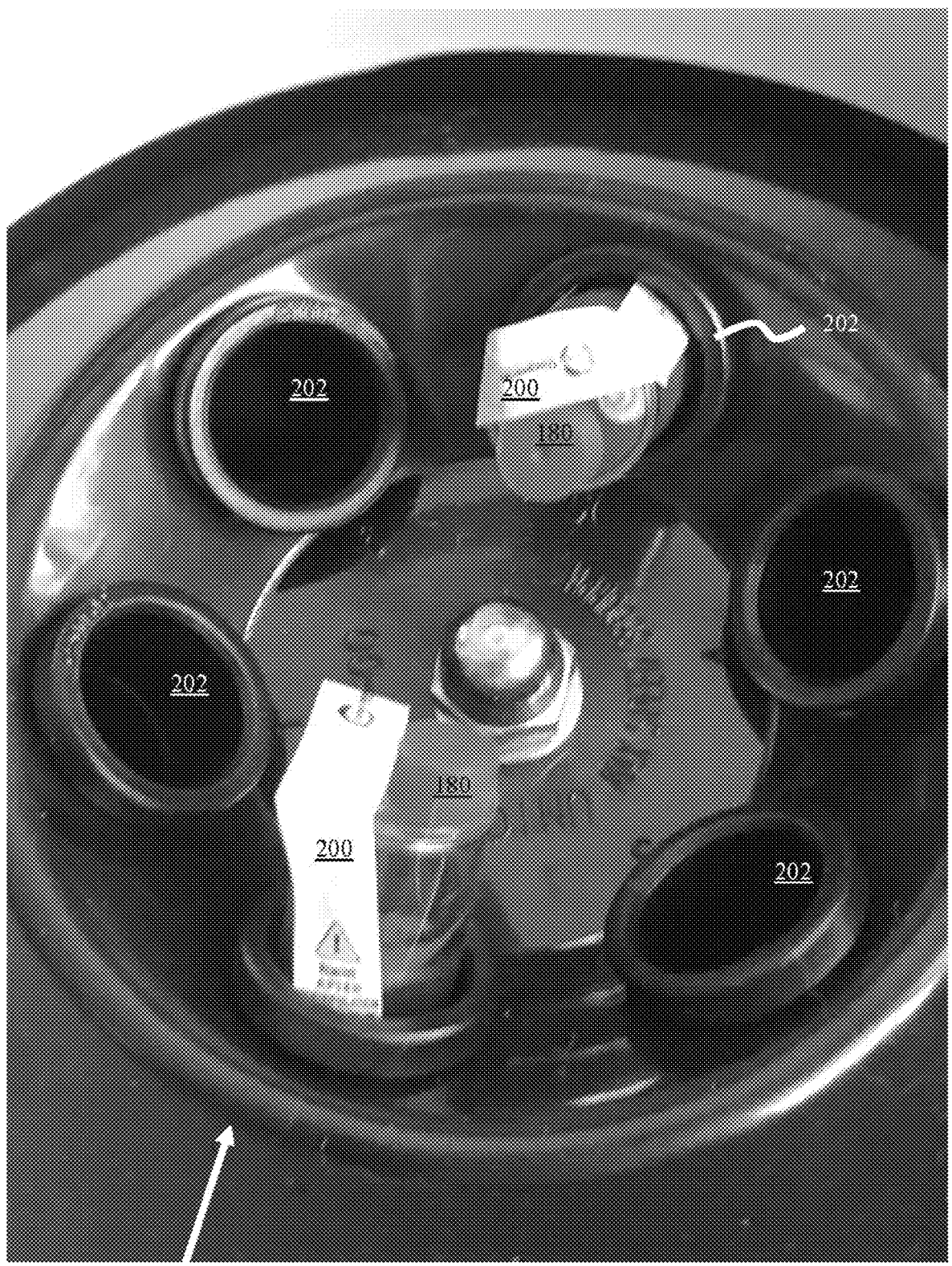
Figure 3S:
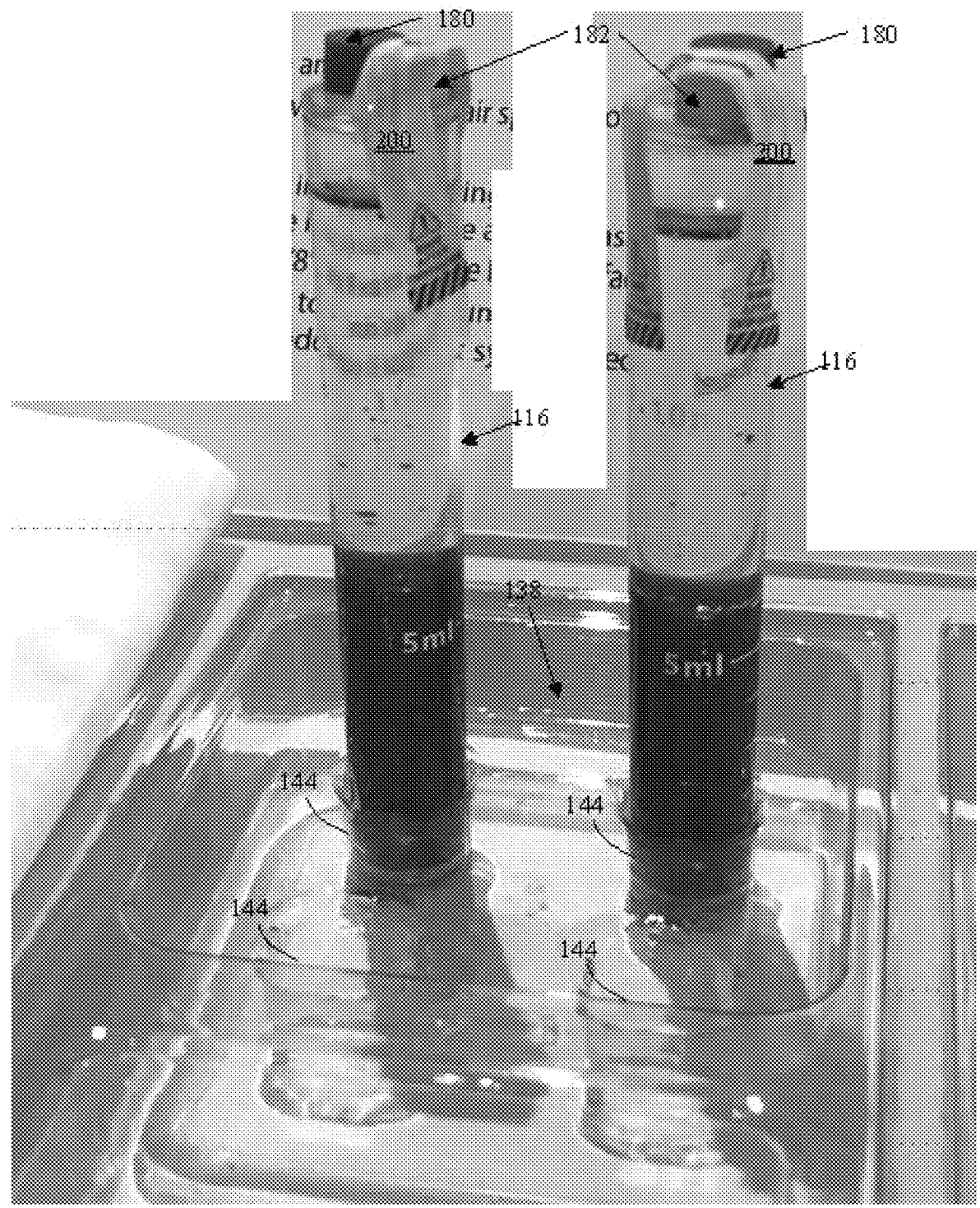

FIGS. 3A to 3S are non-limiting, exemplary illustrations of a second stage of the platelet rich plasma separation kit for filling PRP tubes with blood followed by separation of PRP (e.g., using density gradient centrifugation) in accordance with one or more embodiments of the present invention.

As illustrated in FIGS. 1A to 3S, once first stage 110 operations of separation process of PRP is complete (FIGS. 1A to 2C), cover 104 may be further peeled off of container 106 as shown by arrow 128 in FIG. 3A to expose second stage 112 compartments 138 and 140 and components therein (detailed below), best shown in FIG. 3B.

As illustrated, just as first stage 110, cover 104 is glued to a second stage 112 separation wall 130. This way, third stage 114 is not accidentally exposed prior to completion of tasks for second stage 112.

As further detailed below, second stage 112 includes a second set of sterile components housed within a second set of compartments 138 and 140 exposed only for filling in a PRP tube 116 with aseptically collected blood from first stage 110 and separation of PRP.

The second set of sterile components are comprised of one or more PRP tube 116, and one or more second stage needle 142 positioned in second stage compartment 140. One or more second stage needle 142 may be connected to first stage syringe 122 for injecting the already aseptically collected blood (from first stage 110) into PRP tubes 116 for later separation of PRP using density gradient centrifugation (which may take about 10 minutes). Second stage needle 142 may be connected to first stage syringe 122 after the used butterfly needle 132 is removed from first stage syringe 122.

As further illustrated, second stage 110 further include compartment 138 comprised of retainer wells 144 to securely retain a PRP tube 116 in a vertical orientation (upright) as best shown in FIG. 3C. Retainer wells 144 are configured commensurate with outer circumferential shape of a PRP tube 116 to retain or hold PRP tubes 116 in place in a vertical (upright) position (FIG. 3N).

Detailed structural discussions of PRP tubes 116 are first provided in FIGS. 3D to 3M before continuing with further discussions of second stage 112 processing operations for separation of PRP, which are further detailed below in relation to FIGS. 3N to 3S.

FIGS. 3D to 3M are non-limiting, exemplary illustrations of a PRP tube used in the platelet rich plasma separation kit shown in FIGS. 1A to 3C in accordance with one or more embodiments of the present invention. FIGS. 3E to 3H show second cover 182 fully exposed with a protective cover 200 removed for discussion purposes only.

As illustrated in FIGS. 3D to 3M, a PRP tube 116 is comprised of a generally cylindrical body 146 with a top flat surface 148 and closed, flat bottom end 150 that can hold 15 ml of blood, which is three times larger than conventional PRP tubes. It should be noted any shape PRP tube may be used so long as the form is compatible with a centrifuge bucket. Closed, flat bottom end 150 enables PRP tube 116 to rest on a surface vertically (secure in upright position) without being held so that it does not tilt over.

Further included are segregated openings (or portals) 152 and 154 (FIG. 3I) at top surface 148 for preventing cross-contamination. Segregated portals 152 and 154 are comprised of a first opening 152 for injection of blood into PRP tube 116 (e.g., functioning as an injection portal) shown in FIGS. 3N to 3P using second stage needle 142. A second opening 154 of the segregated portals 152 and 154 is for aspiration of PRP from PRP tube 116 (e.g., functioning as an aspiration portal) shown in FIGS. 4A to 4H).

As further illustrated, PRP tube 116 is comprised of a third opening 156 for maintaining an interior pressure of PRP tube 116 at equilibrium with ambient pressure. Accordingly, third opening 156 functions as a vent.

Third opening 156 may comprise of a through-opening on top surface 148 of PRP tube 116 and covered over by a filter member 158. Filter member 158 may comprise of an antimicrobial filter attached to an interior facing side of third opening 156, equalizing pressure between interior and exterior of PRP tube 116 by allowing air flow while preventing bacteria from entering through the vent and into PRP tube 116. Filter member 158 may be attached to underneath the through-opening 156 (underside of top end) by ultrasonic welding, for example. Filter member may comprise of a mesh having opening spans of approximately 0.2 microns. This means that air within PRP tube 116 may vent out, while preventing bacteria from entering through opening 156 into PRP tube 116. The overall venting structure (combination of opening 156 and filter 158) automatically equalize interior pressure of PRP tube with ambient (or exterior) pressure, which prevents blood spillage, damage to blood cells, and reduces the steps detailed above for injection and aspiration (and hence the time) required to inject blood and or extract PRP.

As best detailed in FIG. 3J-1, first opening 152 and second opening 154 may be comprised of an annular cylindrical projection 160 that extends from top surface 148 of PRP tube 116. It should be noted that although first opening 152 is shown to have larger diameter and or girth in general compared to second opening 154, both openings 152 and 154 may be equal in size and in fact, identical in size and structure as best shown in FIG. 3J-2. Alternatively, second opening 154 may be made larger than first opening 152. Differences in size of first and second openings 152 and 154 is preferred as such a difference would be yet another visual indication to users to distinguish injection portal from aspiration portal.

Annular cylindrical projection 160 includes an inner diameter opening 162 and an outer diameter 164, a difference of which defines a thickness or the body of the annular cylindrical projections 160. An upper portion 166 of annular cylindrical projection 160 is an annular flange 168.

Annular flange 168 has an inner diameter that is the same as inner diameter opening 162 of annular cylindrical projection 160. An outer diameter 170 of annular flange 168 is longer than outer diameter 164 of annular cylindrical projection 160. A height 172 of annular cylindrical projection 160 may be equal to or vary from a height 174 of annular flange 168. As further illustrated, an outer circumference 176 of annular flange 168 includes an outer annular perturbance 178.

FIGS. 3K to 3M are non-limiting, exemplary illustrations of a cover for first and second openings of PRP tube in accordance with one or more embodiments of the present invention. First opening 152 and second opening 154 include color coded respective first (red) color cover 180 and a second (yellow) color cover 182. Differences in color provide a further visual indication to users to distinguish injection portal 152 from aspiration portal 154.

First and the second covers 180 and 182 may comprise of a silicone stopper for easier insertion and passage of lateral aspiration spinal needle 210 (FIG. 4A) through second cover 182 (at third stage 114, detailed below). In this non-limiting, exemplary instance, the silicone stopper may have a shore hardness of about 40 and thickness of about 2 mm. This enable easier insertion of lateral aspiration spinal needle 210 through second over 182 without the lateral aspiration spinal needle 210 bending.

As further detailed below, top exterior 184 of first cover 180 and second cover 182 may include an indexing (or indicator) feature 186 that identifies the proper insertion position of a tip of the respective second stage needle 142 through first cover 180 and a third stage spinal needle 210 (detailed below) through second cover 182. In this non-limiting, exemplary instance, indexing feature 186 may be a concaved section such as a dip (small dimple or depression) on a general center of first cover 180 and second cover 182. Accordingly, indexing feature 186 of first and the second covers 180 and 182 is positioned over a radial center of respective first and second openings 152 and 154. The index features 186 of covers 180 and 182 therefore, directs user to insert second stage needle 142 through first cover 180, passed first central opening 152 or insert third stage needle 210 through second cover 182, passed the second central opening 154 thus avoiding bumping into the solid surface (body or thickness) of the first and the second annular cylindrical projections 160.

As best shown in FIGS. 3K to 3M, first and second covers 180 and 182 are comprised of a cylindrical cap structure (inter bottom 194 shown in FIG. 3M) that cover over annular cylindrical projections 160 of PRP tube 116. An inner wall 188 of the cylindrical cap structure (best shown in FIG. 3K) includes an inner circumferential annular protuberance 190 near a distal end edge 192.

As best shown in FIG. 3J-1, cylindrical cap structure of the first and second covers 180 and 182 cover over annular cylindrical projections 160 of first and second openings 152 and 154 of PRP tube 116. Outer annular perturbance 178 of flange 168 of annular cylindrical projection 160 presses against inner wall 188 of cylindrical cap covers 180 and 182, providing a friction-fit holding strength to secure the cylindrical cap over annular cylindrical projection 160. Inner annular protuberance 190 of cylindrical cap structure of covers 180 and 182 is latched to the underneath surface 196 of flange 168 for added latch holding strength to further secure covers 180 and 182 over openings 152 and 154.

It should be noted that in addition to friction-fit and latch holding strengths, the side of the body of annular cylindrical projections 160 (including sides of flanges 168) may also be covered with well-known medical grade adhesive to further secure first cover 180 onto first opening 152 and second cover 182 onto second opening 154 so that they are not dislodged or dismounted and do not come-off by accident during injection and or aspiration and further, during PRP tube 116 density gradient centrifugation process (detailed below).

The remaining FIGS. 3N to 3S continue discussions with respect to second stage 112 processing operations for separation of PRP. As illustrated in FIGS. 1A to 3S, aseptically collected blood from first stage 110 is injected into PRP tube 116 via first opening 152 through first cover 182 (RED colored). That is, second stage needle 142 is first installed on first stage syringe 122 (that includes aseptically collected blood from first stage 110) and inserted though indexed feature 186 of first cover 180 and into PRP tube 116. Thereafter, the plunger of first stage syringes 122 is pressed to inject blood into PRP tube 116. Note that PRP tubes 116 are vertical secured and positioned within retainer wells 144 of compartment 138 of second stage 112.

Equilibrium between interior pressure of PRP tube 116 and exterior or ambient pressure is maintained while blood is continuously injected into PRP tube 116. As blood is continuously accumulated within PRP tube 116, PRP tube internal air continues to escape through vent 156 to thereby maintain in equilibrium the interior and the exterior pressures.

As best shown in FIGS. 3P and 3Q, blood must not be filled to the very top so that it does not contact the vent filter member 158. If two PRP tubes 116 are used to inject all of the aseptically collected blood from a subject, it would be best if both were filled to the same level so that when they are placed within centrifuge, they balance each other during density gradient centrifugation process.

As part of second stage 112 operations for processing PRP, PRP tubes 116 filled with aseptically collected blood from a subject are positioned inside a centrifuge 198, FIG. 3R. Note that second cover (second silicone stopper) 182 covers over second opening 152 is coved over by protective tape or sticker (e.g., a mylar plastic) 200 with a mild adhesive during this second stage 112 operation of processing PRP.

Protective tape 200 prevents second cover 182 over second opening 154 from being contaminated during centrifugation. This protective tape 200 will remain on second cover 182 until the end of second stage 112 and, will be removed during third stage 114 of operations for processing PRP. This protective tape 200 may be printed with instructions, such as "remove AFTER centrifugation." As indicated above, protective cover 200 is shown as removed in FIGS. 3E to 3H for discussion and teaching purposes only, which are related to the physical structure of second cover 112. Otherwise, protective cover 200 must remain on second cover 182 until the end of second stage 112.

As further shown in FIG. 3R, there is no lid to contact the centrifuge buckets 202 and further, since there is no need for a lid, the overall volume of PRP tube 116 is increase for a tighter fit within centrifuge buckets 202. As best shown in FIG. 3S, after density gradient centrifugation process (which may take several minutes), red blood cells are moved to the bottom of PRP tubes 116 and the PRP on top.

It should be noted that the centrifugal force and duration of centrifugation required to separate PRP will vary depending on many factors, including the size of PRP tube 116, the subject species (e.g., humans, bovine, equine, feline, canine, etc.), and others. As a non-limiting, non-exhaustive example, a PRP tube 116 with an inner diameter 15 mm with a blood of a bovine would require 275 Relative Centrifugal Force (RCF) for a duration of 20 minutes for separation of PRP.

FIGS. 4A to 4H are non-limiting, exemplary illustrations of a third stage of the platelet rich plasma separation kit for aspiration of PRP in accordance with one or more embodiments of the present invention. As illustrated in FIGS. 1A to 4H, third stage 114 that a third set of sterile components housed within a third set of compartments 206 and 208 exposed only for aspirating the PRP from the PRP tubes 116 of second stage 112 (shown in FIGS. 3S and 4A).

Figure 4A:
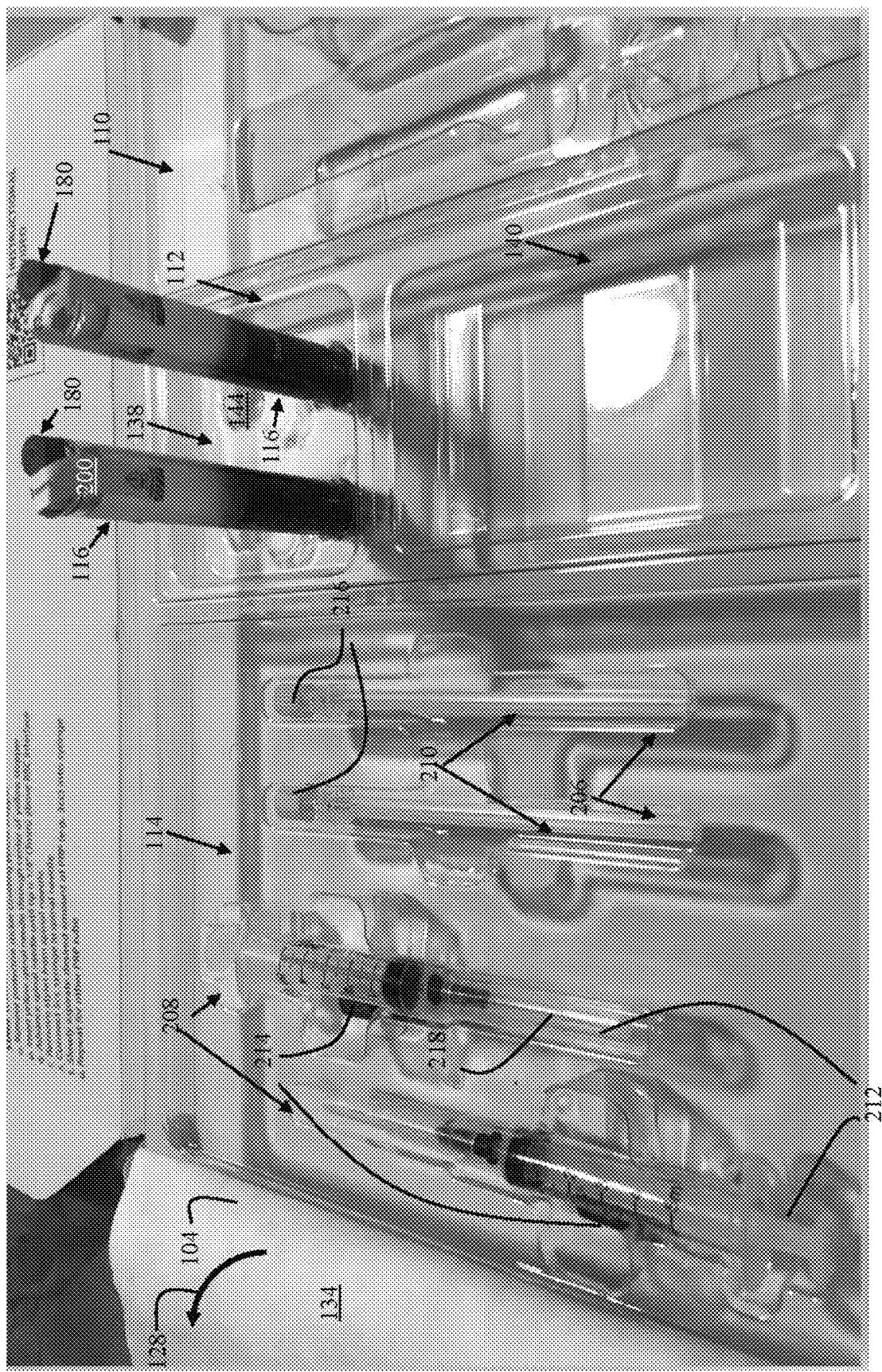
FIGS. 4A to 4H are non-limiting, exemplary illustrations of a third stage of the platelet rich plasma separation kit for aspiration of PRP in accordance with one or more embodiments of the present invention.

As shown in FIG. 4A, once second stage 112 operations of separation process of PRP is complete (FIGS. 1A to 3S), cover 104 may be further peeled off of container 106 as shown by arrow 128 in FIG. 4A to expose third stage 114 compartments 206 and 208 and components therein (detailed below).

The third set of sterile components are comprised of one or more lateral aspiration spinal needle 210, one or more third stage syringe (plunger, barrel, and needle) 212, and one or more luer caps 214. Critical and advantageous reason for housing spinal needle 210 within the third set of compartments of third stage 114 is that they are needed at third stage 114 and not prior and hence, they would not unnecessarily be exposed to non-sterile environment for a longer duration then need be.

Lateral aspiration spinal needle 210 has a lateral opening (perpendicular to the longitudinal axis of needle) for lateral aspiration of PRP. Non-limiting, non-exhaustive examples of lateral aspiration spinal needle 210 may include a Whitacre spinal needle, Sprotte spinal needle, or the like. These types of needle are used to control aspiration of PRP with or without white blood cells at the users choosing, depending how deep lateral aspiration needle 210 is inserted within the separated blood. Spinal needle 210 is inserted through second silicone cover 182 and advanced until its tip is situated in the plasma.

After centrifuge, white blood cells (which have a lesser specific gravity value than red blood cells) normally accumulate in between the red blood cells at the bottom of the PRP tube 116 and the rest of the plasma at the top. White blood cells have a greater specific gravity value than platelets. The interface section between red blood cells and platelet rich plasma (which also includes white cells) is also known as the buffy coat. In general, large amounts of platelets accumulate on, and just above, the buffy coat layer.

The drawback with the use of conventional longitudinal aspiration spinal needles is that their orifice opening is at the end of the needle and is oriented longitudinally downward, which would pull in the white blood cells off of the red blood cell interface. Therefore, conventionally, to avoid aspiration of white blood cells, users would have to position orifice opening of the conventional longitudinal aspiration spinal needle above the visible red blood cells (about 5 mm or so), which is above buffy coat layer. The problem with the conventional method is that this (5 mm distance) would also leave behind large amounts of PRP. Accordingly, one or more embodiments of the present invention use lateral aspiration spinal needles 210 instead with orifice opening oriented laterally. The lateral oriented orifice opening would pull in (or suck) platelets slightly above the buffy coat layer while minimizing white blood cells (positioned underneath). If the user desires white blood cells in the PRP then the spinal needle is advanced into the buffy coat.

Figure 4B:
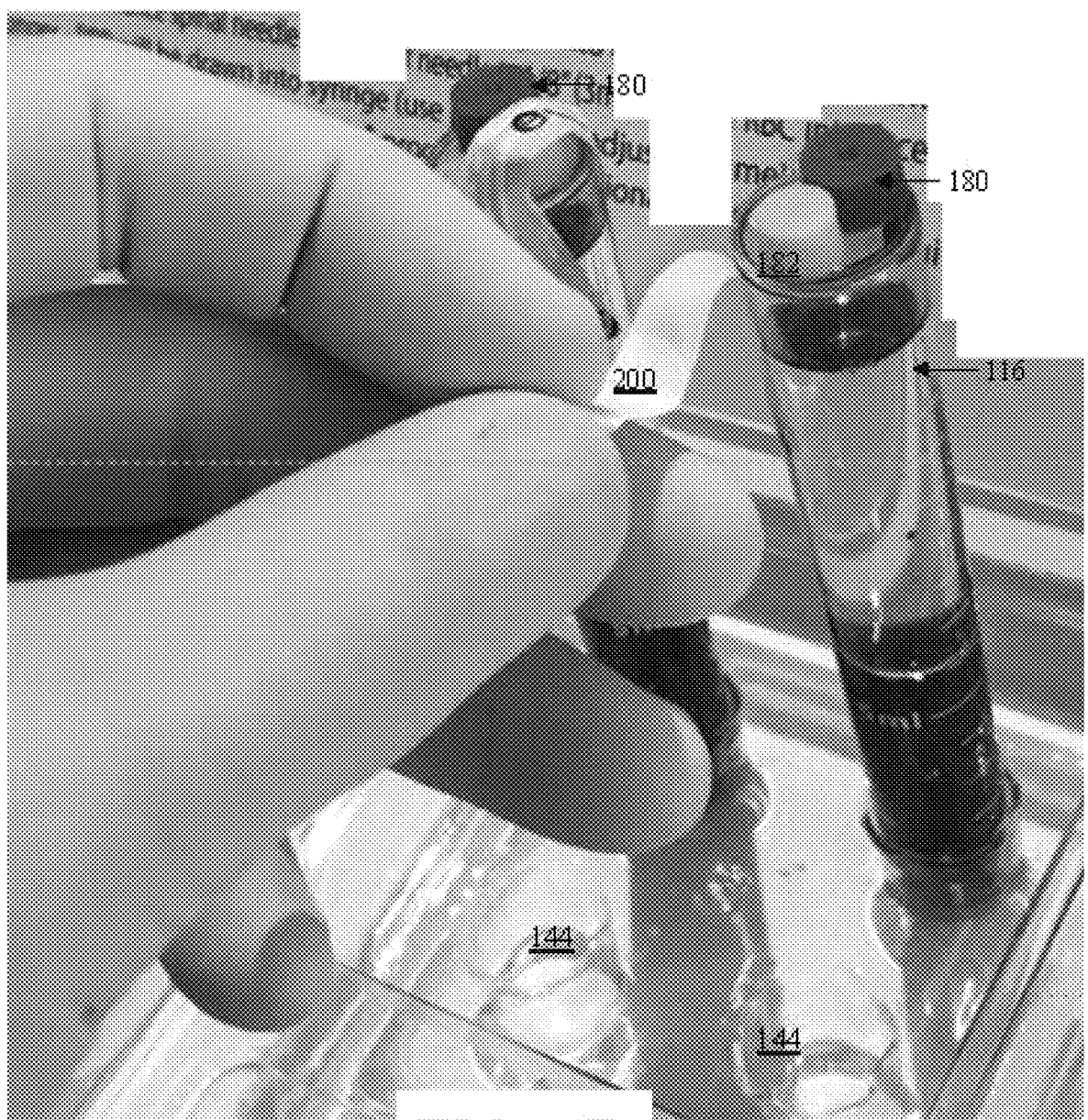
Figure 4C:
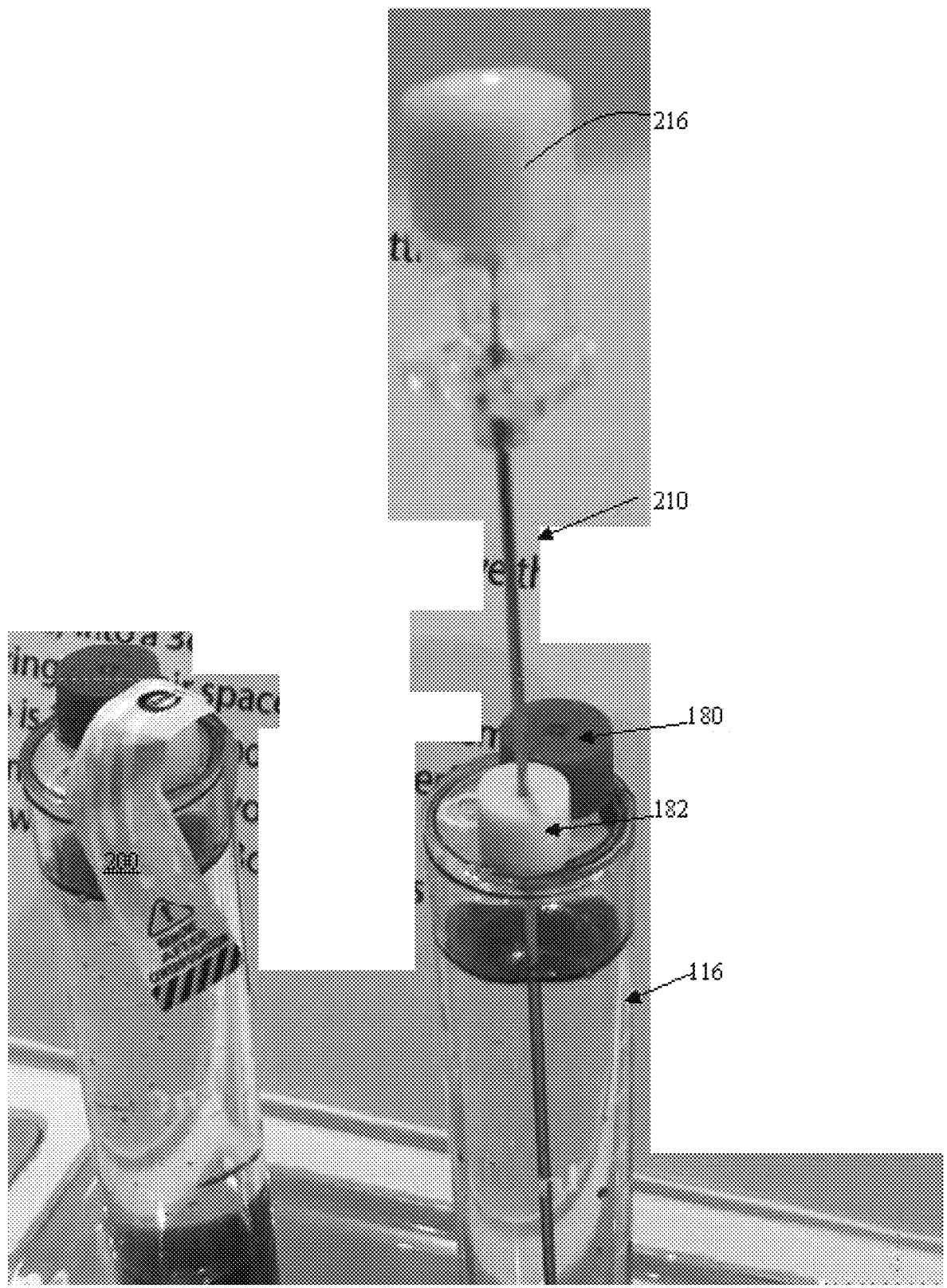

As illustrated in FIG. 4B, protective tape 200 of second cover 182 is removed during third stage 114. Spinal needle 210 (while having the stylet 216) is accessed from compartment 206 of third stage 114 and is inserted into PRP tube 116 via second cover 182 to pass through second opening 154 (FIG. 4C). Please note that stylet 216 has a yellow color, matching the color of yellow for second cover 182.

Figure 4D:
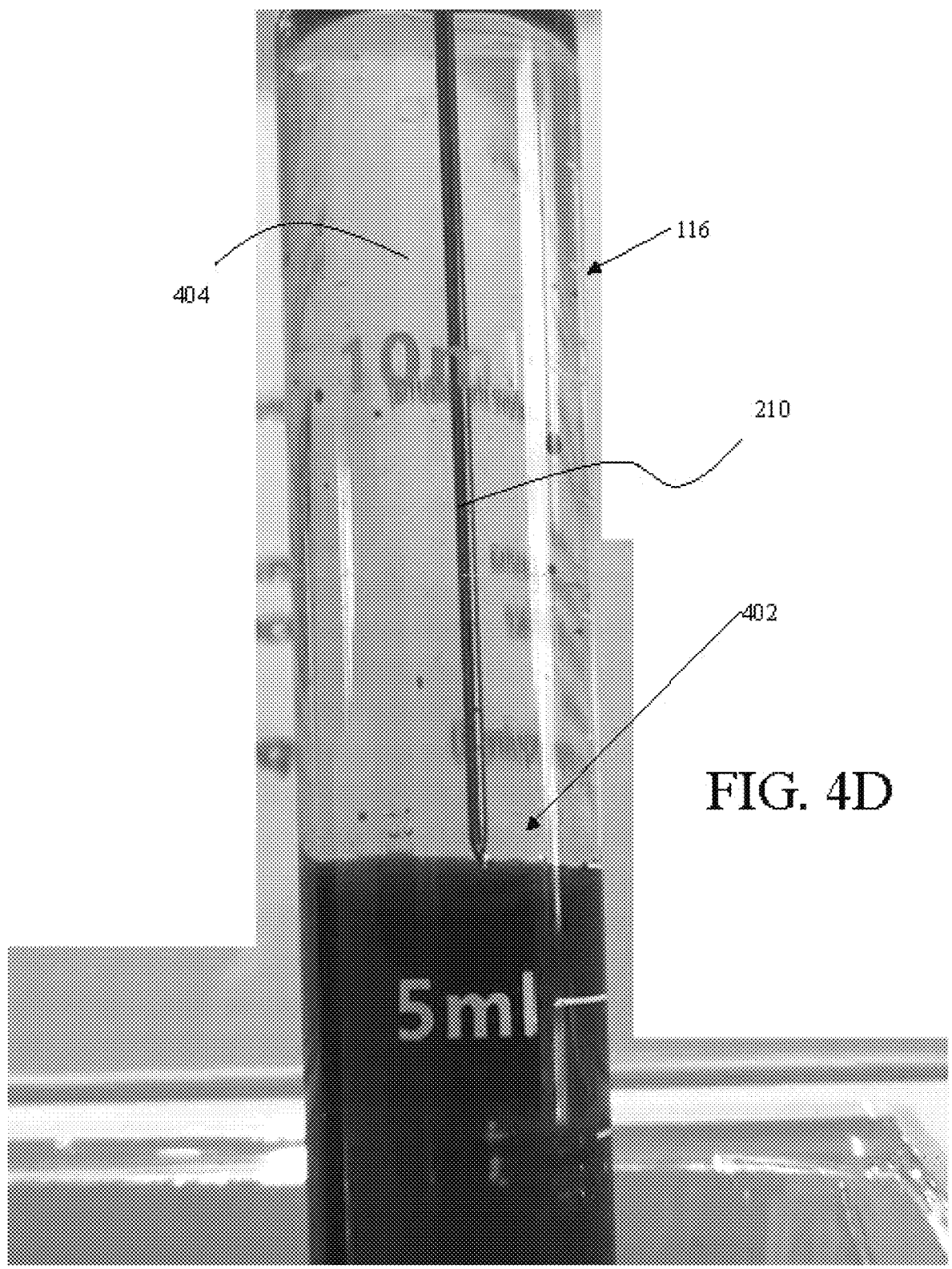

Spinal needle 210 is advanced (lowered) within PRP tube 116 to a selected position 402 (FIG. 4D) for aspiration of PRP 404 only or PRP with white blood cells. If no white blood cells are to be aspirated, a tip of spinal needle 210 may be stopped above the buffy coat and the red blood cells interface 402. (FIG. 4D).

Figure 4E:
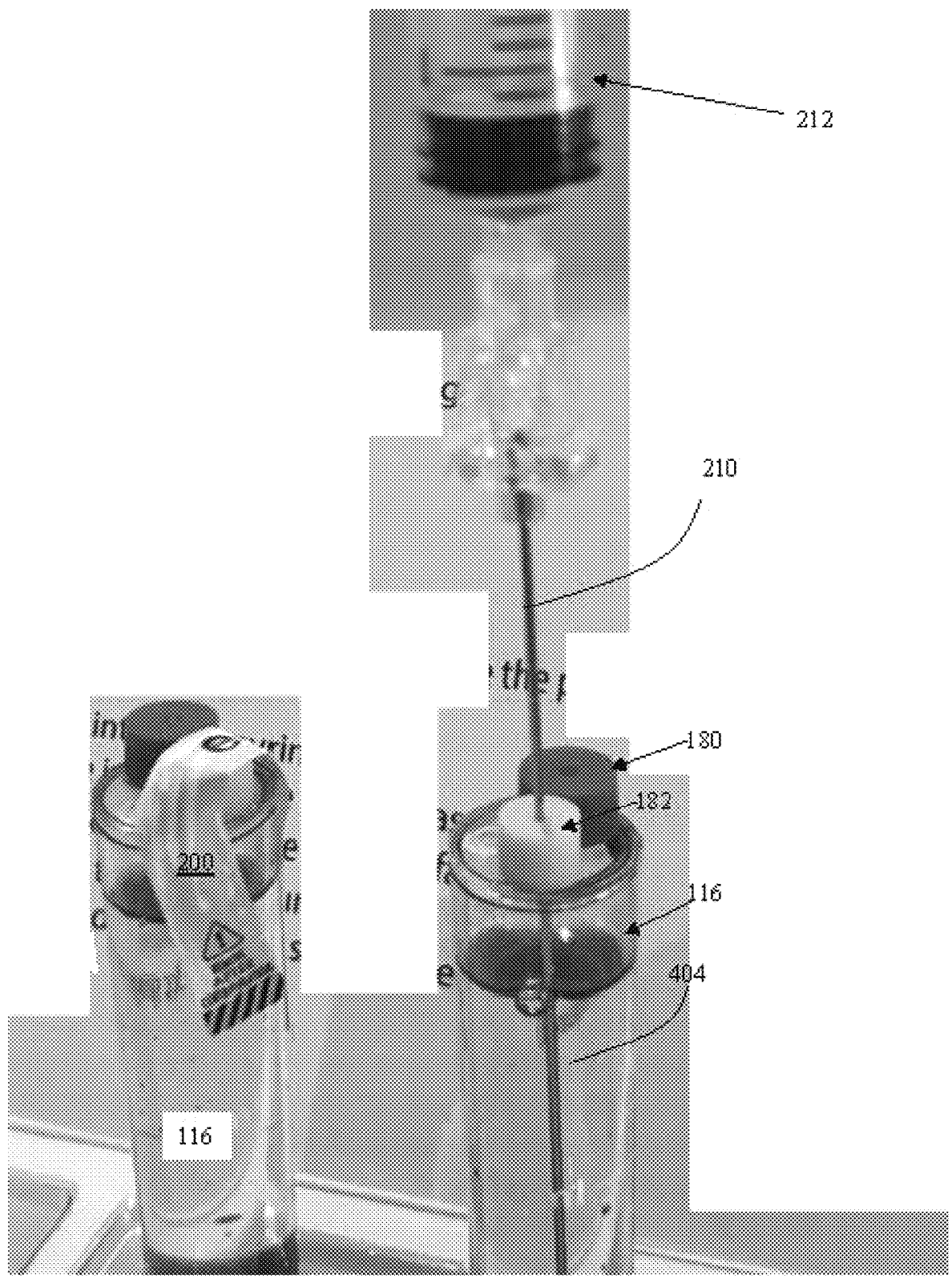
Figure 4F:
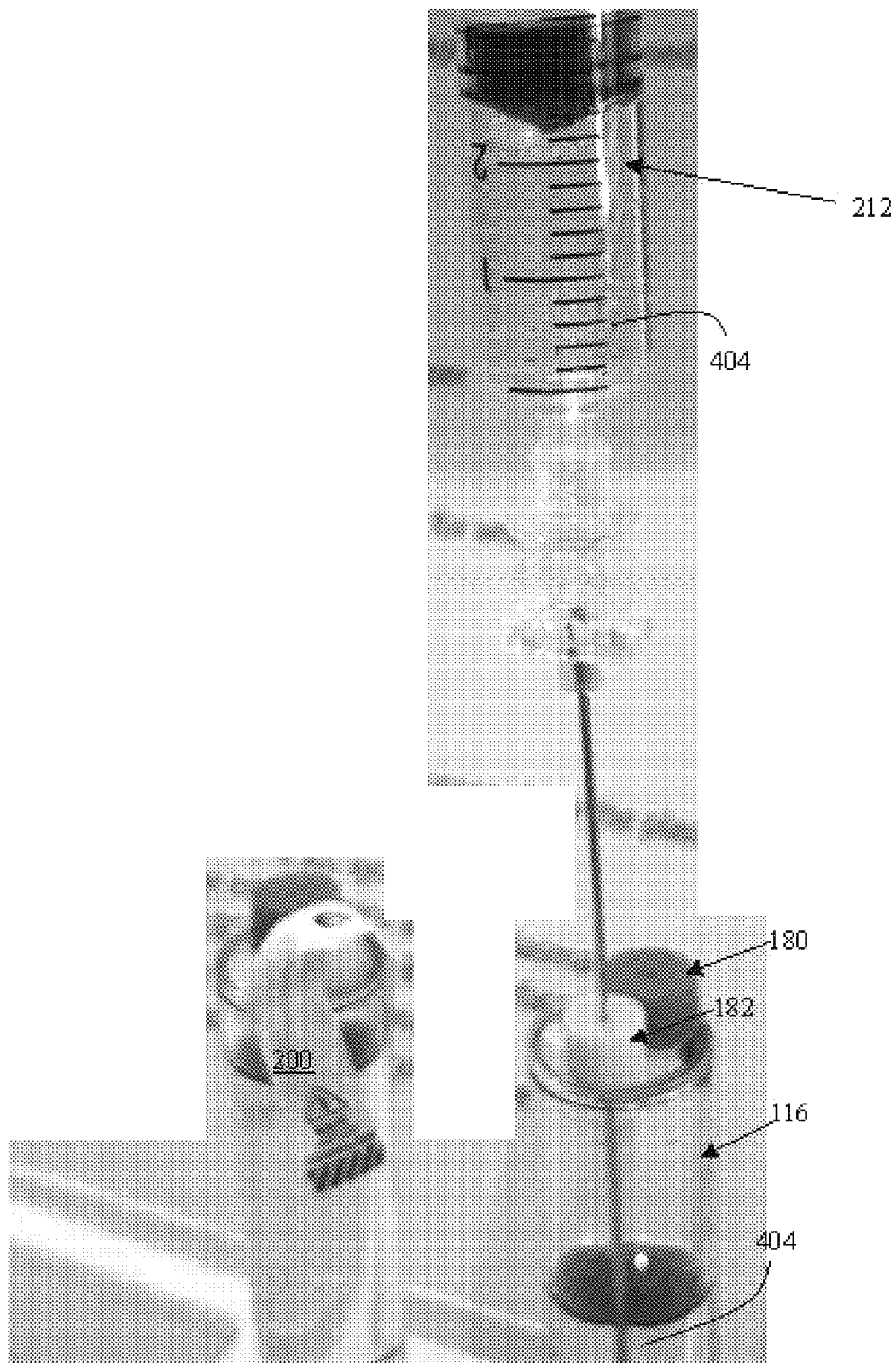

A third stage syringe 212 is connected to spinal needle 210 (after the stylet 216 is removed) for aspiration of PRP 404 only or PRP 404 with while blood cells (FIGS. 4E and 4F). Please note that at this stage, the third stage actual needles 218 of third stage syringe 212 must be removed first so to enable third stage syringe 212 to be connected to spinal needle 210. Thereafter, third stage syringe 212 is disconnected from spinal needle 210 and needle 218 is reconnected with third stage syringe 212.

Figure 4G:
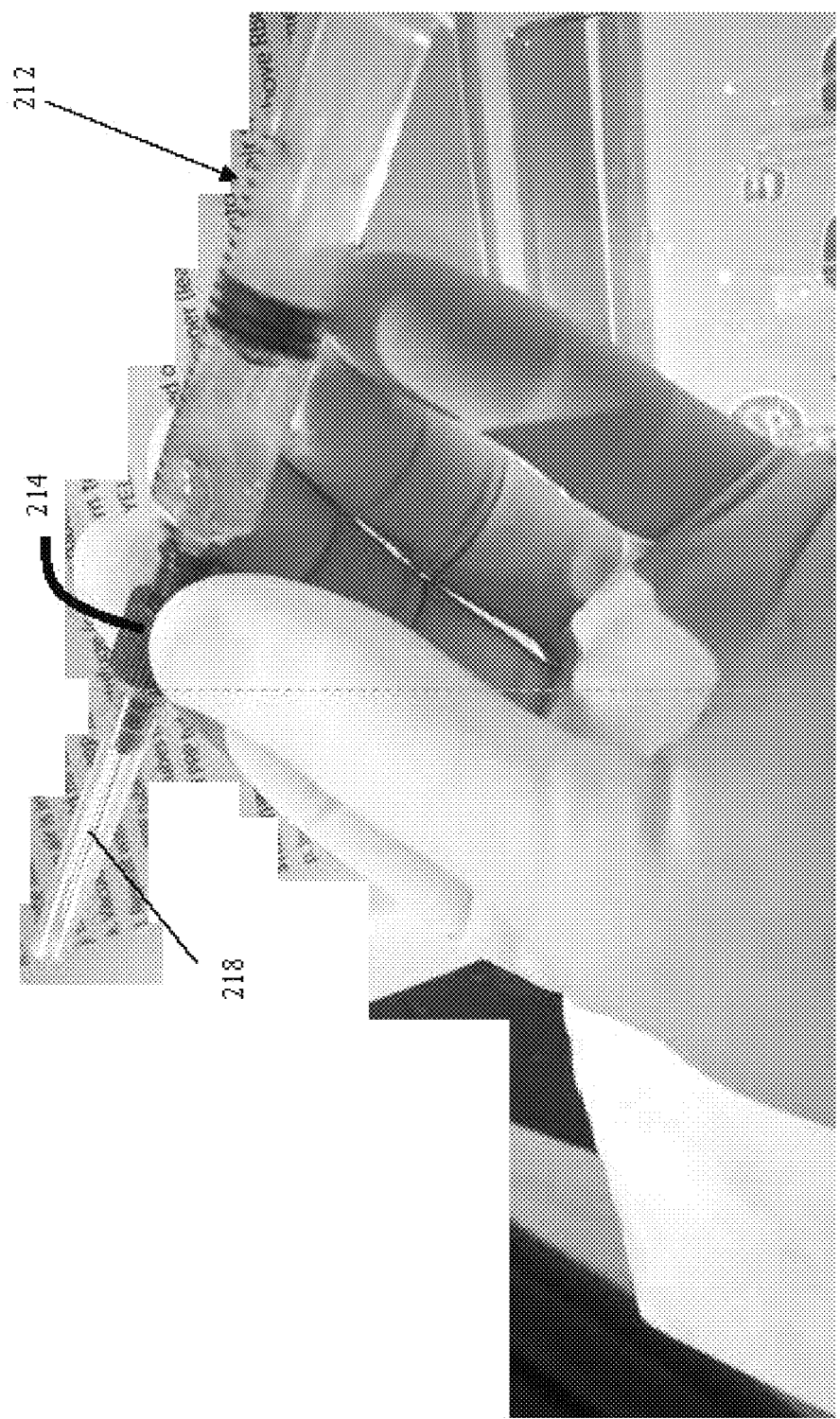
Figure 4H:
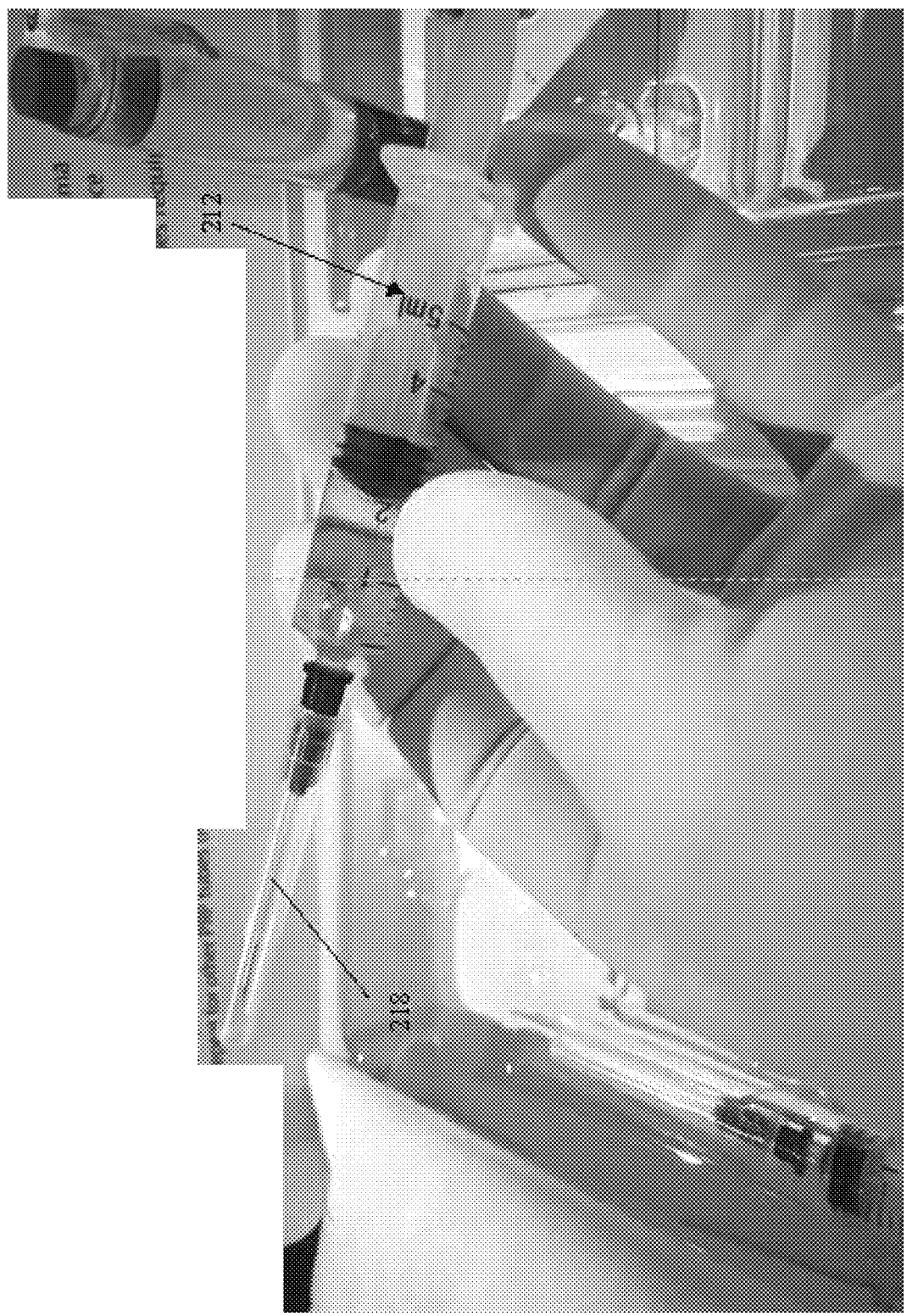

A luer cap 214 to cover over needle 218 of third stage syringe 212 is used in the case the subject is not ready for injection (FIG. 4G). Luer cap 214 prevents leakage of content from the barrel of syringe 212. Once subject is ready, luer cap 214 may be removed for injection of extracted PRP (FIG. 4H) using needles 218.

FIGS. 5A to 5F are non-limiting, exemplary illustrations of a platelet rich plasma separation kit for aspiration of PRP in relation to humans in accordance with one or more embodiments of the present invention. Kit 300 illustrated in FIGS. 5A to 5F includes similar corresponding or equivalent components, methods, interconnections, functional, operational, and or cooperative relationships as the kit 100 that is shown in FIGS. 1A to 4H, and described above. Therefore, for the sake of brevity, clarity, convenience, and to avoid duplication, the general description of FIGS. 5A to 5F will not repeat every corresponding or equivalent component, methods, interconnections, functional, operational, and or cooperative relationships that has already been described above in relation to kit 100 that is shown in FIGS. 1A to 4H but instead, are incorporated by reference herein.

As illustrated in FIGS. 5A to 5F, platelet rich plasma separation kit 300 for aspiration of PRP in relation to humans includes four PRP tubes 116 (in compartment 140) in second stage 112, 4 third stage syringes 212 (in compartment 208) in third stage 114, and four third stage safety needles 218 (in compartment 304) and four luer caps 214 (compartment 302) in third stage 114.

In this embodiment, all syringes (barrel and plunger) for all stages 110, 112, and 114 have luer lock type barrels with plungers. Further, all needles for all three stages 110, 112, and 114 are well known safety needles.

Figure 5A:
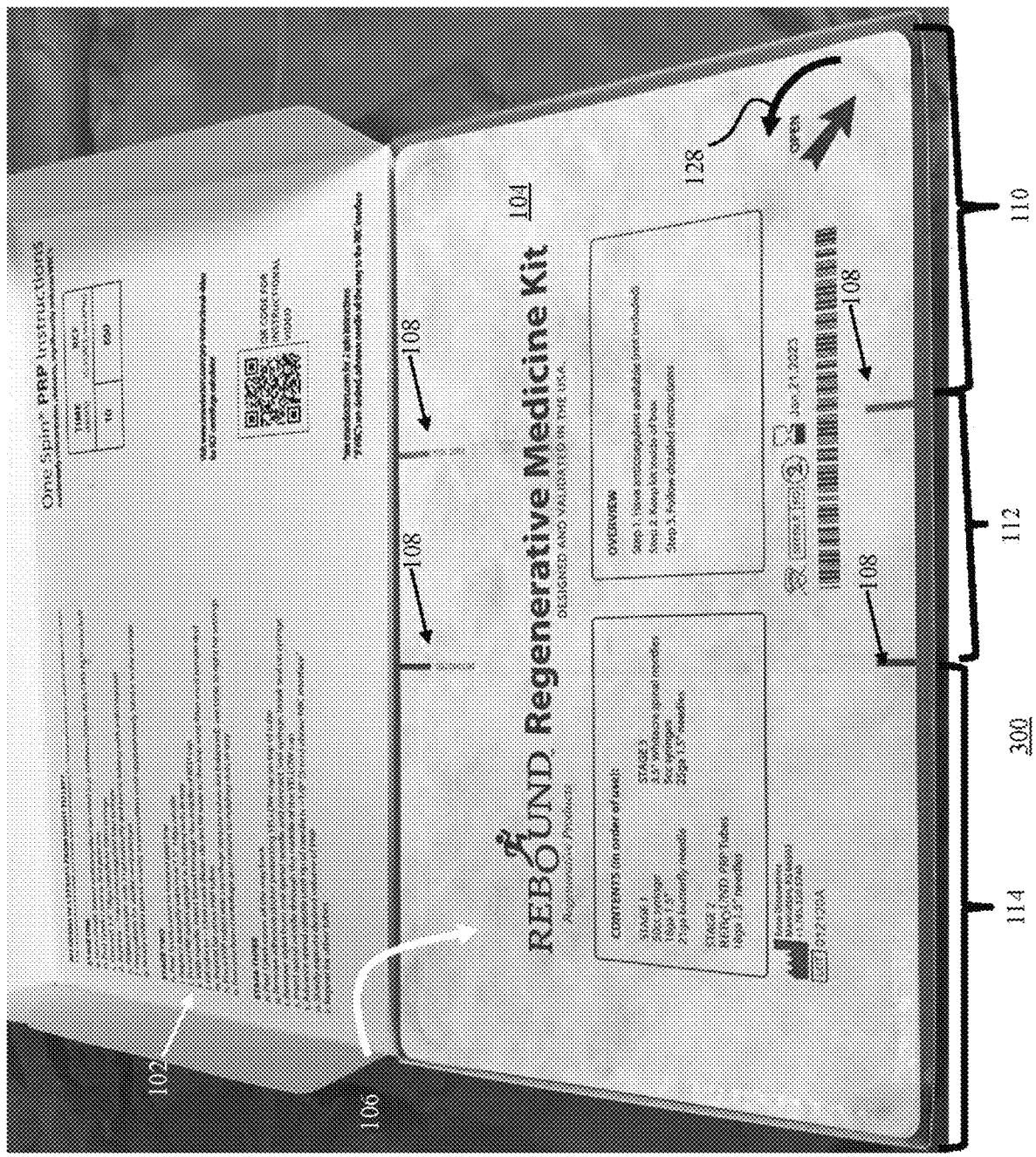
FIGS. 5A to 5F are non-limiting, exemplary illustrations of a platelet rich plasma separation kit for aspiration of PRP in relation to humans in accordance with one or more embodiments of the present invention.
Figure 5B:
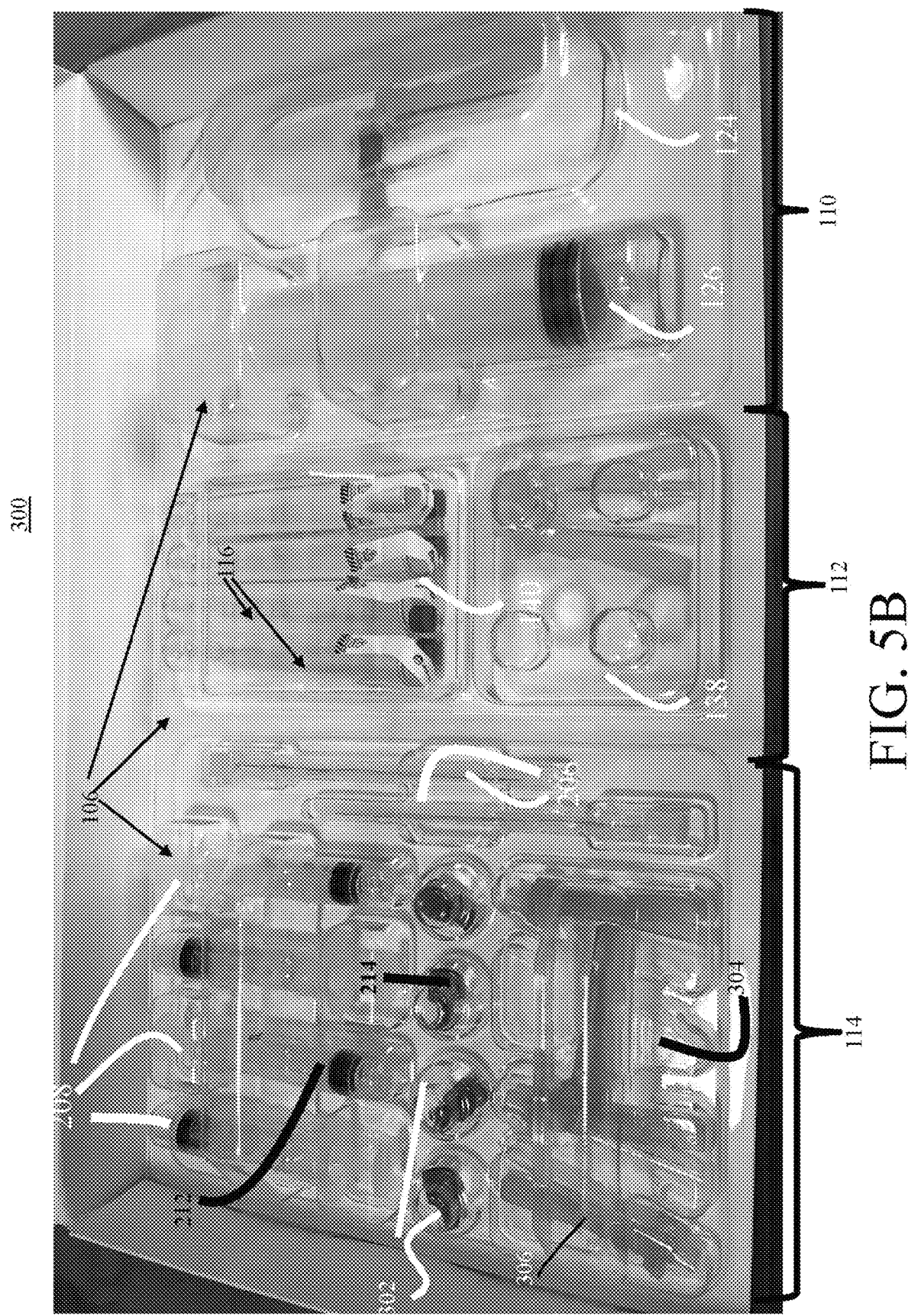
Figure 5C:
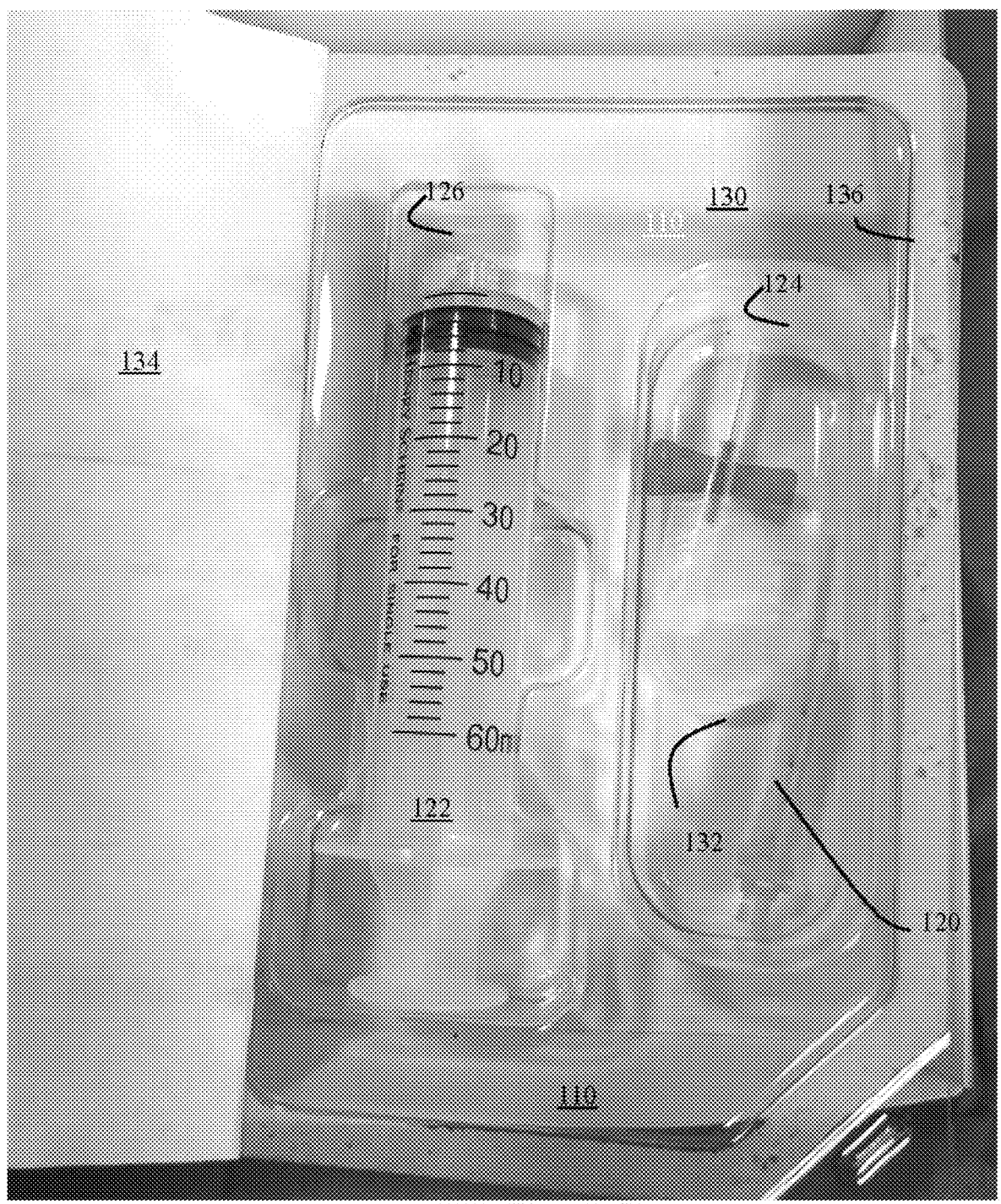

As detailed in FIG. 5C, first set of sterile components of first stage 110 include a first syringe (plunger and barrel) 122 in compartment 126. In this non-limiting, exemplary instance, first syringe 122 may comprise of a 60 cc syringe. Larger volume syringe would produce larger volume of PRP. Further included is safety needle 120 and a 21 ga butterfly safety needle 132 in compartment 124 of first stage 110.

Figure 5D:
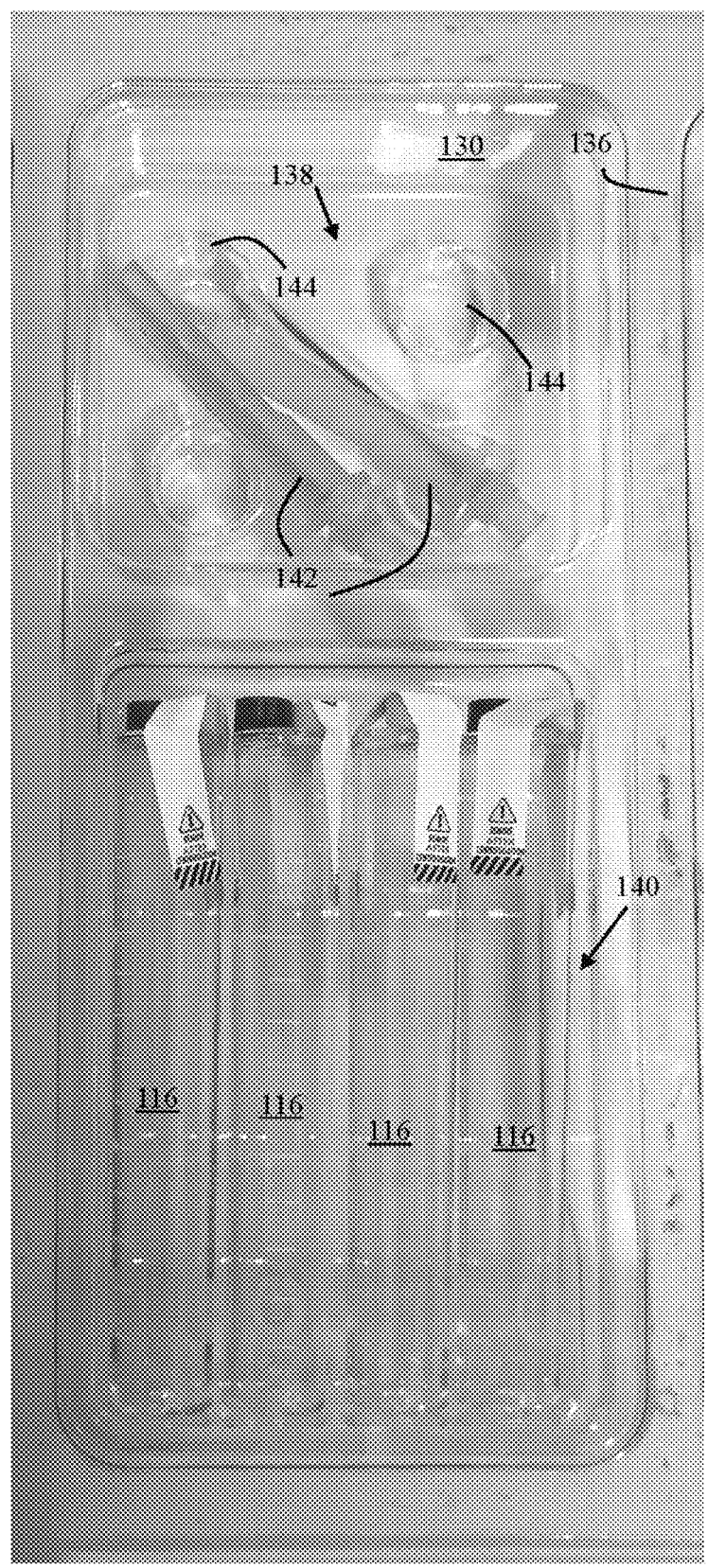
Figure 5E:
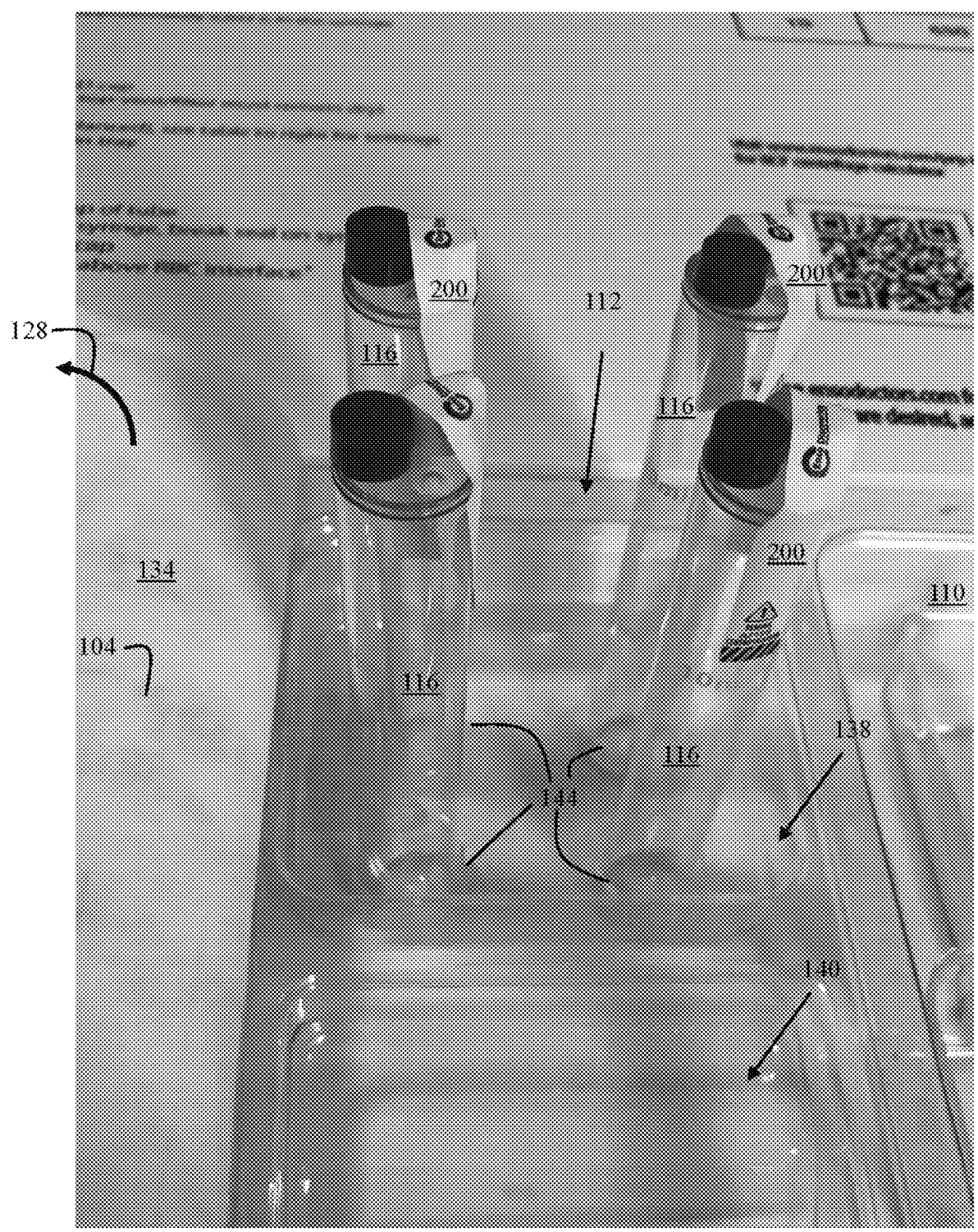

As detailed in FIG. 5D, second set of sterile components of second stage 112 includes four PRP tubes 116 in compartment 140 and two safety needles 142 in compartment 138. FIG. 5E is a non-limiting, exemplary illustration of four PRP tubes 116 of second stage 112 positioned and secured with retainer wells 144, ready for injection of for aseptic collected blood from first stage 110.

Figure 5F:
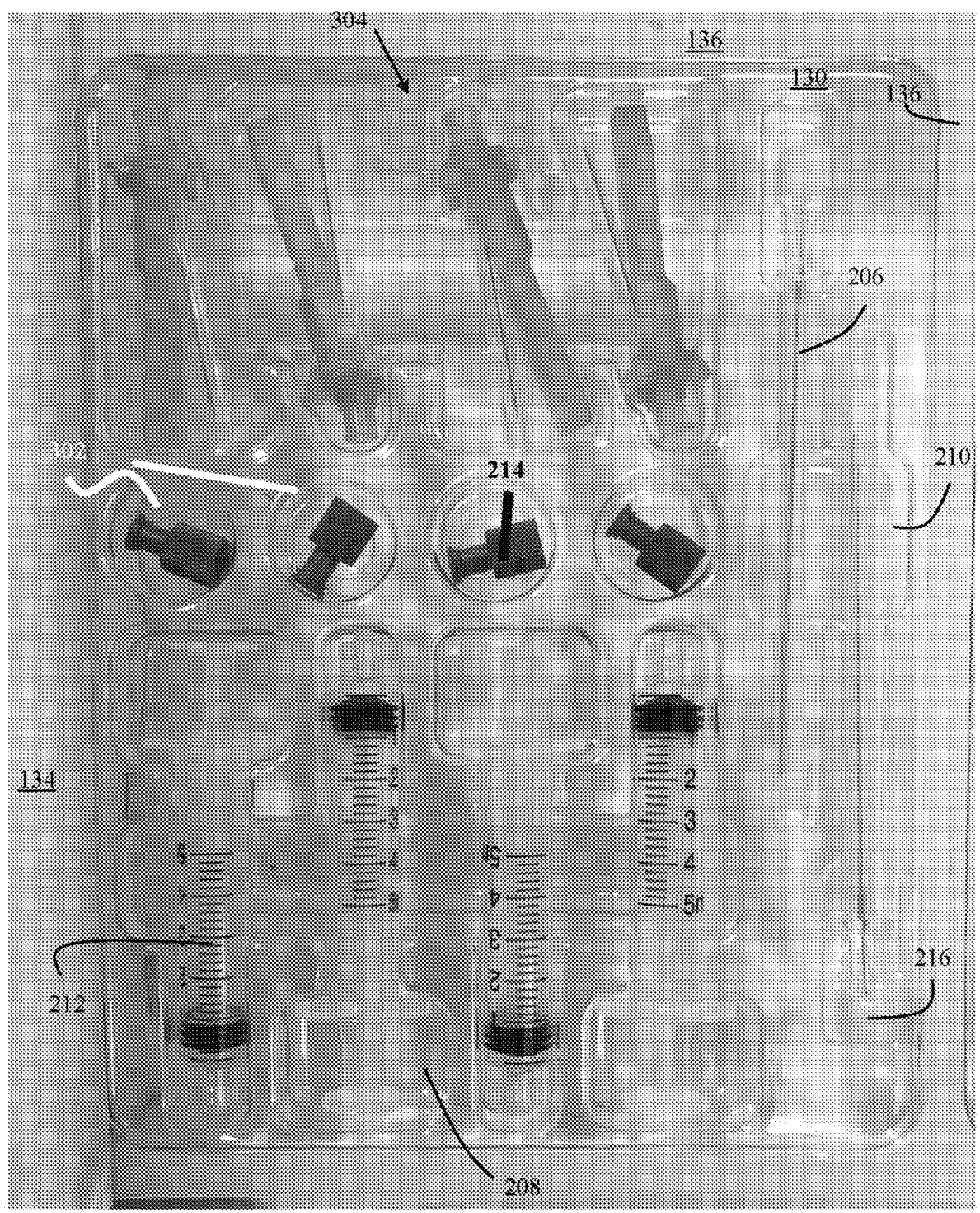

As detailed in FIG. 5F, third set of sterile components of third stage 114 includes four third stage needles 218 (which are safety needles) in compartment 304, and four 5 ml third stage syringes 212 in compartment 208, for four luer caps 214 in compartment 302, and two lateral aspiration spinal needle 210 in compartment 206.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Further, the specification is not confined to the disclosed embodiments. Therefore, while exemplary illustrative embodiments of the invention have been described, numerous variations and alternative embodiments will occur to those skilled in the art. For example, the kits may be provided in different sizes. Small kit may have a single 30 ml syringe (first stage 110) with 2 PRP tubes 116 (second stage 112). Large kits may have 60 ml syringe and 4 PRP tubes 116. Such variations and alternate embodiments are contemplated, and can be made without departing from the spirit and scope of the invention.

It should further be noted that throughout the entire disclosure, the labels such as left, right, front, back, top, inside, outside, bottom, forward, reverse, clockwise, counter clockwise, up, down, or other similar terms such as upper, lower, aft, fore, vertical, horizontal, lateral, oblique, proximal, distal, parallel, perpendicular, transverse, longitudinal, etc. have been used for convenience purposes only and are not intended to imply any particular fixed direction, orientation, or position. Instead, they are used to reflect relative locations/positions and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

Further the terms "a" and "an" throughout the disclosure (and in particular, claims) do not denote a limitation of quantity, but rather denote the presence of at least one of the referenced item.

The use of the phrases "and or," "and/or" throughout the specification (if any used) indicate an inclusive "or" where for example, A and or B should be interpreted as "A," "B," or both "A and B."

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. A sterile platelet rich plasma (PRP) separation kit comprising:
   a compartmentalized container having a cover that allows for a stage-specific exposure of sterile components of the sterile PRP separation kit housed within stage-specific compartments to a non-sterile environment commensurate with a specific stage of operation of a separation process of PRP;
   the cover is detachably secured to top surfaces of stage separation walls of stage specific compartments of the compartmentalized container to ensure stage-specific isolation and stage-specific exposure of sterile components;
   a first stage that includes a first set of sterile components housed within a first set of compartments and exposed only when and for aseptic collection of blood while a second stage and a third stage remain unexposed to the non-sterile environment;
   with the first set of sterile components comprising:
   a first stage syringe;
   a first stage needle; and
   a winged infusion set;
   the second stage that includes a second set of sterile components housed within a second set of compartments and exposed only when and for filling in a PRP tube with aseptically collected blood from the first stage while the third stage remains unexposed to the non-sterile environment;
   with the second set of sterile components comprising:
   the PRP tube; and
   the second stage needle that is connected to the first stage syringe for injecting the aseptically collected blood into the PRP tube for separation of PRP;
   a third stage that includes a third set of sterile components housed within a third set of compartments and exposed only when and for aspirating the PRP from the PRP tubes of the second stage;
   with the third set of sterile components comprising:
   a lateral aspiration spinal needle;
   a third stage syringe with a third stage needle; and
   a syringe cap.

2. The sterile platelet rich plasma separation kit as set forth in claim 1, wherein:
   the PRP tube is comprised of:
   cylindrical body with a top flat surface and bottom flat surface;
   segregated openings at the top surface for preventing cross-contamination;
   the segregated openings are comprised of:
   a first opening for injection of blood into the PRP tube;
   a second opening for aspiration of PRP from the PRP tube; and
   a third opening for maintaining an interior pressure of the PRP tube at equilibrium with ambient pressure.

3. The sterile platelet rich plasma separation kit as set forth in claim 2, wherein:
   the third opening is a vent.

4. The sterile platelet rich plasma separation kit as set forth in claim 3, wherein:
   the vent is a through-opening covered over by a filter.

5. The sterile platelet rich plasma separation kit as set forth in claim 4, wherein:
   the filter is an anti-microbial filter attached to an interior facing side of the vent, equalizing pressure between interior and exterior of the PRP tube by allowing air flow while preventing bacteria from entering through the vent and into the PRP tube.

6. The sterile platelet rich plasma separation kit as set forth in claim 2, wherein:
   the first opening and the second opening include respective first and second covers.

7. The sterile platelet rich plasma separation kit as set forth in claim 6, wherein:
the first and the second covers are comprised of a silicone for easier insertion and passage of the lateral aspiration spinal needle.

8. The sterile platelet rich plasma separation kit as set forth in claim 7, wherein:
the silicone has a shore hardness of about 40 and thickness of about 2 mm.

9. The sterile platelet rich plasma separation kit as set forth in claim 6, wherein:
an exterior of the first and the second covers includes an indexing feature that identifies a proper insertion position of a tip of a needle through the first and the second covers.

10. The sterile platelet rich plasma separation kit as set forth in claim 9, wherein:
the indexing feature of the first and the second covers is over a radial center of the respective the first and the second openings.

11. The sterile platelet rich plasma separation kit as set forth in claim 6, wherein:
the first and the second covers are further comprised of:
a cylindrical cap structure that cover over annular cylindrical projections of the PRP tube;
an inner wall of the cylindrical cap includes an inner circumferential annular protuberance near a distal end edge of the cylindrical cap.

12. The sterile platelet rich plasma separation kit as set forth in claim 2, wherein:
first opening and the second opening are comprised of:
an annular cylindrical projection that extends from a top surface of PRP tube.

13. The sterile platelet rich plasma separation kit as set forth in claim 12, wherein:
the annular cylindrical projection includes an inner diameter opening and an outer diameter.

14. The sterile platelet rich plasma separation kit as set forth in claim 12, wherein:
an upper portion of the annular cylindrical projection includes a flange.

15. The sterile platelet rich plasma separation kit as set forth in claim 14, wherein:
the flange is an annular flange with an inner diameter that equals an inner diameter of the annular cylindrical projection, and an outer diameter that is longer than an outer diameter of the annular cylindrical projection.

16. The sterile platelet rich plasma separation kit as set forth in claim 11, wherein:
an outer circumference of the flange includes an outer annular perturbance.

17. A sterile platelet rich plasma (PRP) separation kit, comprising:
a compartmentalized container having a cover that allows for a stage-specific exposure of sterile components of the sterile PRP separation kit housed within stage-specific compartments to a non-sterile environment commensurate with a specific stage of operation of a separation process of PRP
the cover is detachably secured to top surfaces of stage separation walls of stage specific compartments of the compartmentalized container to ensure stage-specific isolation and stage-specific exposure of sterile components;
a first stage for aseptic collection of blood;
a second stage for separation of PRP within a PRP tube; and
a third stage for aspirating the PRP from the PRP tube of the second stage;
wherein:
the PRP tube is comprised of:
segregated openings that include:
a first opening for injection of blood into the PRP tube;
a second opening for aspiration of PRP from the PRP tube; and
a third opening for maintaining an interior pressure of the PRP tube at equilibrium with ambient pressure.

\* \* \* \* \*